(12) United States Patent
Greaves et al.

(10) Patent No.: US 7,288,122 B2
(45) Date of Patent: Oct. 30, 2007

(54) CATIONIC DIAZO COMPOUNDS, COMPOSITIONS COMPRISING THEM AS DIRECT DYE, PROCESS FOR DYEING KERATIN FIBERS AND DEVICE THEREFOR

(75) Inventors: Andrew Greaves, Montevrain (FR); Hervé David, Joinville le Pont (FR)

(73) Assignee: L'Oreal S.A., Paris (FR)

( * ) Notice: Subject to any disclaimer, the term of this patent is extended or adjusted under 35 U.S.C. 154(b) by 266 days.

(21) Appl. No.: 11/159,242

(22) Filed: Jun. 23, 2005

(65) Prior Publication Data

US 2006/0005324 A1 Jan. 12, 2006

Related U.S. Application Data

(60) Provisional application No. 60/588,042, filed on Jul. 15, 2004.

(30) Foreign Application Priority Data

Jun. 23, 2004 (FR) .................................. 04 06870

(51) Int. Cl.
  *A61K 7/13* (2006.01)
(52) U.S. Cl. ........................ 8/405; 8/406; 8/407; 8/408; 8/410; 8/437; 8/571; 8/573; 8/574; 548/318.1; 548/321.1; 548/400; 546/184; 546/249; 534/608
(58) Field of Classification Search .................... 8/405, 8/406, 407, 408, 410, 437, 571, 573, 574; 548/318.1, 321.1, 400; 546/184, 249; 534/608
See application file for complete search history.

(56) References Cited

U.S. PATENT DOCUMENTS

| | | | |
|---|---|---|---|
| 3,151,106 | A | 9/1964 | Tsang et al. |
| 4,003,699 | A | 1/1977 | Rose et al. |
| RE30,199 | E | 1/1980 | Rose et al. |
| 4,563,191 | A | 1/1986 | Hähnke et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Möckli |
| 5,766,576 | A | 6/1998 | Löwe et al. |
| 5,792,221 | A | 8/1998 | Lagrange et al. |
| 5,852,179 | A | 12/1998 | Dado |
| 6,099,593 | A | 8/2000 | Terranova et al. |
| 6,284,003 | B1 | 9/2001 | Rose et al. |
| 6,645,258 | B2 | 11/2003 | Vidal et al. |
| 6,884,265 | B2 | 4/2005 | Vidal et al. |
| 7,208,586 | B2 * | 4/2007 | Greaves et al. ............. 534/608 |
| 2004/0244124 | A1 | 12/2004 | Plos et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 044 059 | 1/1982 |
| EP | 0 714 954 | 6/1996 |
| EP | 0 770 375 | 5/1997 |
| EP | 1 133 976 | 9/2001 |
| FR | 2 586 913 | 3/1987 |
| FR | 2 692 572 | 12/1993 |
| FR | 2 733 749 | 11/1996 |
| FR | 2 750 048 | 12/1997 |
| GB | 1026978 | 4/1966 |
| GB | 1153196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078596 | 10/2002 |
| WO | WO 02/078596 A2 * | 10/2002 |
| WO | WO 02/100366 | 12/2002 |

OTHER PUBLICATIONS

STIC Search Report dated May 10, 2007.*
Erwin Buncel and Sam-Rok Keum, "Studies of Azo and Azoxy Dyestuffs-16. Investigations of the Protonation and Tautomeric Equilibria of 4-(p'-Hydroxyphenylazo)pyridine and Related Substrates," Tetrahedron, vol. 39, No. 7, pp. 1091-1101 (1983).
Mohammad H. Habibi, "Efficient Catalytic Oxidation of Primary Aromatic Amines to Azo Derivatives by Manganese (III) Tetraphenylporphyrin," J. Chem. Research, Issue. 10, pp. 648-649 (1998).
Ikenna Onyido and Collins I. Ubochi, "Heteroaromatic Azo-Activated Nucleophilic Substitutions. The Reaction of 4-(p-Methoxyphenylazo)pyridinium Methiodide with Piperidine in Dimethyl Sulphoxide," Heterocycles, vol. 26, No. 2, pp. 313-317 (1987).
Xiao-Yang Wang et al., "The Preparation of Symmetrical Azobenzenes from Anilines by Phase Transfer Catalyzed Method," Synthetic Communications, vol. 29, No. 13, pp. 2271-2276 (1999).
Siegfried Hünig and Gert Köbrich, "Synthese von 1-substitulerten Pyridon-(4)-hydrazonen," Liebigs Ann,. Chem., 617, pp. 180-202 (1958).
English language DERWENT abstract of EP 0 770 375.
English language DERWENT abstract of JP 2-19576.
English language DERWENT abstract of JP 5-163124.
French Search Report dated Feb. 15, 2005, for FR 0406872 (French Priority Application for co-pending U.S. Appl. No. 11/159,267) Examiner Kirsch.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The present disclosure relates to cationic diazo dye compounds of formula (I):

$$\text{Dye1-LK-Dye2,} \qquad (I)$$

dye compositions comprising the direct dye compounds, and also to a process for dyeing keratin fibers using this composition and a multi-compartment kit.

24 Claims, No Drawings

OTHER PUBLICATIONS

French Search Report dated Feb. 16, 2005, for FR 0406871 (French Priority Application for co-pending U.S. Appl. No. 11/159,154) Examiner Kirsch.

French Search Report dated Feb. 16, 2005, for FR 0406870 (French Priority Application for U.S. Appl. No. 11/159,242, the present application) Examiner Kirsch.

French Search Report dated Feb. 16, 2005, for FR 0406869 (French Priority Application for co-pending U.S. Appl. No. 11/159,237) Examiner Kirsch.

Co-pending U.S. Appl. No. 11/159,267, Title: Cationic Diazo Compounds Compositions Comprising Them as Direct Dyes, Process for Dyeing Keratin Fibers and Device Therefor Inventors: Andrew Greaves et al. U.S. Filing Date: Jun. 23, 2005.

Co-pending U.S. Appl. No. 11/159,154, Title: A Cationic Diazo Compound, Compositions Comprising at Least One Cationic Diazo Compound as Direct Dye, A Process for Dyeing Keratin Fibers and Device Therefor Inventors: Andrew Greaves et al. U.S. Filing Date: Jun. 23, 2005.

Co-pending U.S. Appl. No. 11/159,237, Title: Cationic Diazo Compounds, Compositions Comprising Them as Direct Dye, Procss for Dyeing Keratin Fibers and Device Therefor Inventors: Andrew Greaves et al. U.S. Filing Date: Jun. 23, 2005.

* cited by examiner

CATIONIC DIAZO COMPOUNDS, COMPOSITIONS COMPRISING THEM AS DIRECT DYE, PROCESS FOR DYEING KERATIN FIBERS AND DEVICE THEREFOR

This application claims benefit of U.S. Provisional Application No. 60/588,042, filed Jul. 15, 2004, the contents of which are incorporated herein by reference. This application also claims benefit of priority under 35 U.S.C. § 119 to French Patent Application No. 04 06870, filed Jun. 23, 2004, the contents of which are also incorporated herein by reference.

The present disclosure relates to specific cationic diazo compounds, to dye compositions comprising such compounds as direct dye in a medium that is suitable for dyeing keratin fibers, and also to a process for dyeing keratin fibers using this composition, as well as a multi-compartment device.

It is known practice to dye keratin fibers, for instance human keratin fibers such as the hair, with dye compositions comprising direct dyes. These compounds are colored and coloring molecules with affinity for the keratin fibers. It is known practice, for example, to use direct dyes of the nitrobenzene type, anthraquinone dyes, nitropyridines and dyes of the azo, xanthene, acridine, azine or triarylmethane type.

These dyes are usually applied to the fibers, optionally in the presence of at least one oxidizing agent if it is desired to obtain simultaneous lightening of the fibers. Once the period of leave-in time has elapsed, the fibers are rinsed, optionally washed and dried.

The colorations resulting from the use of direct dyes are temporary or semi-permanent colorations. The nature of the interactions that bind the direct dyes to the keratin fiber, and their desorption from the surface and/or the core of the fiber, are responsible for their poor dyeing power and their poor relative resistance to washing or to perspiration, compared with permanent dye colorations.

An additional difficulty can also arise, associated with the fact that in order to obtain a particular color, it is necessary in most if not all cases to mix together several dyes. However, each dye may not have the same affinity for the fibers, which is reflected either by heterogeneous colorations or by changes in color over time, for example after washing the fibers at least one time, exposure to sunlight, etc.

Therefore, there is a need in the art to provide direct dyes that do not have one or more of the drawbacks that may occur with the existing direct dyes.

Accordingly, one aspect of the present disclosure relates to direct dyes with which varied shades can be obtained without the problem of changes in color over time.

The present disclosure also relates to novel cationic diazo compounds chosen from those of formula (I), and the acid addition salts thereof:

Dye1-LK-Dye2     (I)

in which Dye1 and Dye2 are, respectively:

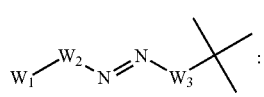

Dye 1

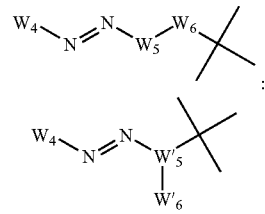

Dye 2 wherein:

$W_1$ and $W'_6$, which may be identical or different, are chosen from $-NR_1R_2$ and $-OR_3$ groups, wherein $R_1$, $R_2$ and $R_3$, which may be identical or different, are chosen from hydrogen atoms and saturated and unsaturated, aromatic and non-aromatic, optionally substituted $C_1$-$C_{20}$, such as $C_1$-$C_{16}$, hydrocarbon-based chains, which can form at least one optionally substituted 3- to 7-membered carbon-based ring, optionally interrupted with at least one hetero atom or with at least one group bearing at least one hetero atom, for instance chosen from oxygen and nitrogen; $R_1$ and $R_2$ possibly forming, with the nitrogen atom to which they are attached, an optionally substituted 5- or 7-membered heterocycle optionally comprising another nitrogen or non-nitrogen hetero atom;

the radicals $R_1$, $R_2$ or $R_3$ of $W'_6$, independently of each other, may optionally form, with part of the group LK and with the nitrogen or oxygen atom to which each is attached, a saturated or unsaturated, aromatic or non-aromatic, optionally substituted 5- to 7-membered heterocycle;

$W_6$ is chosen from $-NR'_1-$ groups and $-O-$ atoms, wherein $R'_1$ is chosen from a hydrogen atom, saturated and unsaturated, aromatic and non-aromatic, optionally substituted $C_1$-$C_{20}$, such as $C_1$-$C_{16}$, hydrocarbon-based chains, which can form at least one optionally substituted 3- to 7-membered carbon-based ring, optionally interrupted with at least one hetero atoms or with at least one group bearing at least one hetero atom, for instance chosen from oxygen and nitrogen;

the radical $R^1_1$ of $W_6$ may optionally form, with the nitrogen atom to which it is attached and a part of the group LK, a saturated or unsaturated, aromatic or non-aromatic, optionally substituted 5- to 7-membered heterocycle optionally comprising another hetero atom chosen from nitrogen and oxygen;

$W_2$, $W_5$ and $W'_5$, which may be identical or different, are chosen from groups of formulae (a), (b), and (c):

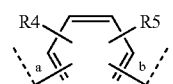
(a)

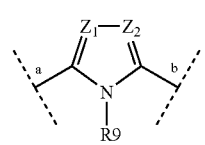
(b)

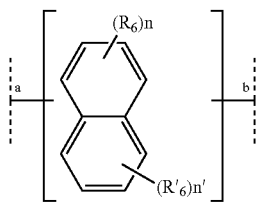
(c)

wherein:
X₁ is chosen from a nitrogen atom and $CR_7$ groups;
X₂ is chosen from a nitrogen atom and $CR_8$ groups;
Z₁ is chosen from a nitrogen atom and $CR_{10}$ groups;
Z₂ is chosen from a nitrogen atom and $CR_{11}$ groups;
$R_4$, $R_5$, $R_6$, $R'_6$, $R_7$, $R_8$, $R_{10}$ and $R_{11}$, which may be identical or different, are chosen from:
  linear and branched, saturated and unsaturated, aromatic and non-aromatic, optionally substituted $C_1$-$C_{16}$ hydrocarbon-based chains, which can form at least one optionally substituted 3- to 6-membered carbon-based ring, optionally interrupted with at least one hetero atom or with at least one group bearing at least one hetero atom, for instance chosen from oxygen and nitrogen;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals;
  alkylcarbonyloxy radicals (RCO—O—) in which R is chosen from $C_1$-$C_4$ alkyl radicals;
  amino groups,
  amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR—) wherein the radicals R, which may be identical or different, are chosen from $C_1$-$C_4$ alkyl radicals;
  carbamoyl groups ((R)₂N—CO) in which the radicals R, which may be identical or different, are chosen from hydrogen atoms and $C_1$-$C_4$ alkyl radicals;
  ureido groups (N(R)₂—CO—NR'—) wherein the radicals R and R', which may be identical or different, are chosen from hydrogen atoms and $C_1$-$C_4$ alkyl radicals;
  sulfonamide groups ((R)₂N—SO₂—) in which the radicals R, which may be identical or different, are chosen from hydrogen atoms and $C_1$-$C_4$ alkyl radicals;
  alkylsulfonylamino groups (RSO₂—NR'—) in which the radicals R and R', which may be identical or different, are chosen from hydrogen atoms and $C_1$-$C_4$ alkyl radicals;
  guanidinium groups ((R')₂N—C(=NH₂⁺)—NR—) in which the radicals R and R', which may be identical or different, are chosen from hydrogen atoms and $C_1$-$C_4$ alkyl radicals;
  nitro groups;
  cyano groups;

halogen atoms, such as chlorine or fluorine;
$R_4$, $R_5$, $R_7$, $R_8$, $R_{10}$ and $R_{11}$ may be a hydrogen atom;
$R_4$, $R_5$, $R_6$, $R'_6$, $R_7$, $R_8$, $R_{10}$ and $R_{11}$, independently of each other, may optionally form, with all or some of the groups $W_1$ or $W'_6$, a saturated or unsaturated, optionally substituted 5- to 7-membered heterocycle;
a bond from $W'_5$ to $W'_6$ or to the group LK;
a represents the bond from $W_2$, $W_5$, or $W'_5$ to the azo group —N=N—;
b represents the bond from $W_2$ to $W_1$, from $W_5$ to $W_6$, or from $W'_5$ to $W'_6$;
$R_9$ is chosen from:
  a hydrogen atom,
  linear and branched, saturated and unsaturated, aromatic and non-aromatic, optionally substituted $C_1$-$C_{16}$ hydrocarbon-based chains, which can form at least one optionally substituted 3- to 7-membered carbon-based ring,
n and n' are integers and their sum is less than or equal to 6; with the proviso that when the sum of n and n' is less than 6, each missing substituent is a hydrogen atom;
$W_3$ and $W_4$, which may be identical or different, are cationic heteroaromatic radicals chosen from those of formulae (1) to (11):

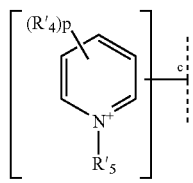
(1)

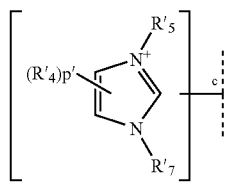
(2)

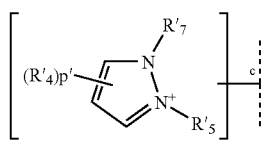
(3)

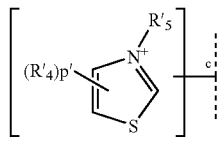
(4)

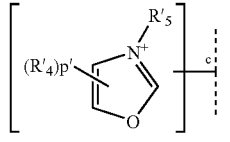
(5)

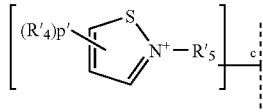
(6)

-continued

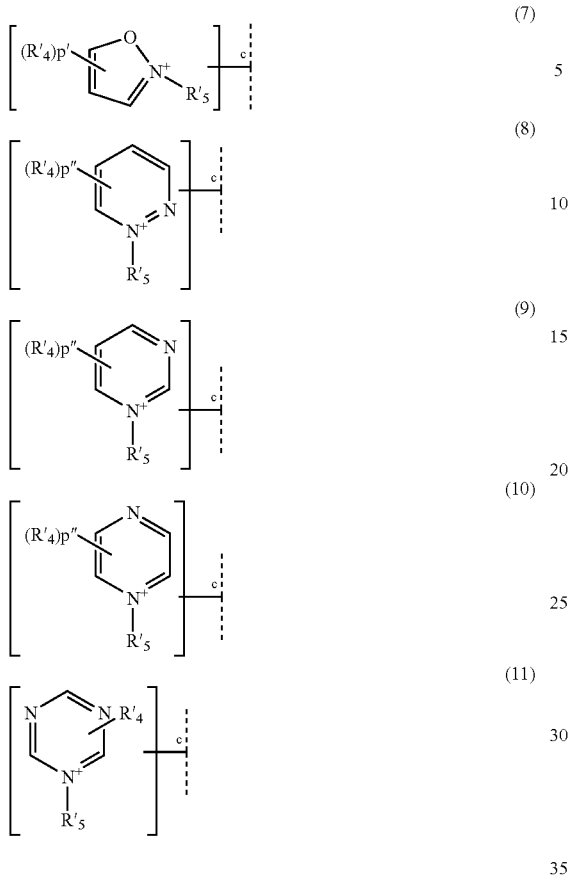

wherein:
R'$_4$, which may be identical or different, substituting the main ring, are chosen from:
  linear and branched, saturated and unsaturated, aromatic and non-aromatic, optionally substituted C$_1$-C$_{16}$ hydrocarbon-based chains, which can form at least one 3- to 6-membered carbon-based ring, optionally interrupted with at least one hetero atom or with at least one group bearing at least one hetero atom, for instance chosen from oxygen and nitrogen;
  hydroxyl groups,
  C$_1$-C$_4$ alkoxy groups,
  C$_2$-C$_4$ (poly)hydroxyalkoxy groups;
  alkoxycarbonyl groups (RO—CO—) in which R is chosen from C$_1$-C$_4$ alkyl radicals,
  alkylcarbonyloxy radicals (RCO—O—) in which R is chosen from C$_1$-C$_4$ alkyl radicals;
  amino groups,
  amino groups substituted with at least one C$_1$-C$_4$ alkyl radical, independently of each other, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR'—) in which the radical R is chosen from C$_1$-C$_4$ alkyl radicals and the radical R' is chosen from a hydrogen atom and C$_1$-C$_4$ alkyl radicals;
  carbamboyl groups ((R)$_2$N—CO—) in which the radicals R, which may be identical or different, are chosen from a hydrogen atom and C$_1$-C$_4$ alkyl radicals;
  ureido groups (N(R)$_2$—CO—NR'—) wherein the radicals R and R', which may be identical or different, are chosen from hydrogen atoms and C$_1$-C$_4$ alkyl radicals;
  sulfonamide groups ((R)$_2$N—SO$_2$—) in which the radicals R, which may be identical or different, are chosen from hydrogen atoms and C$_1$-C$_4$ alkyl radicals;
  alkylsulfonylamino groups (RSO$_2$—NR'—) in which the radicals R and R', which may be identical or different, are chosen from hydrogen atoms and C$_1$-C$_4$ alkyl radicals;
  guanidinium groups ((R')$_2$N—C(=NH$_2^+$)—NR—) in which the radicals R and R', which may be identical or different, are chosen from hydrogen atoms and C$_1$-C$_4$ alkyl radicals;
  nitro groups;
  cyano groups;
  halogen atoms, such as chlorine or fluorine;
  two radicals R'$_4$ borne by two adjacent carbon atoms of the main ring may optionally form an aromatic or non-aromatic, 5- or 6-membered secondary ring, optionally substituted with at least one hydrogen; at least one hydroxyl group; at least one C$_1$-C$_4$ alkyl radical; at least one C$_1$-C$_4$ alkoxy radical; at least one C$_2$-C$_4$(poly)hydroxyalkoxy radical; at least one amino radical; and/or at least one amino radical substituted with at least one C$_1$-C$_4$ alkyl radical, which may be identical or different, optionally bearing at least one hydroxyl group; for instance, the secondary ring may be a 6-membered aromatic ring optionally substituted as indicated above;
R'$_5$, borne by the quaternized nitrogen atom, in the case of W$_4$ is chosen from linear and branched, saturated and unsaturated, aromatic and non-aromatic, optionally substituted C$_1$-C$_{16}$ hydrocarbon-based chain, which can form at least one optionally substituted 3- to 6-membered carbon-based ring, optionally interrupted with at least one hetero atom or with at least one group bearing at least one hetero atom, such as oxygen or nitrogen; the radical R'$_5$ is such that the atom directly linked to the quaternized nitrogen atom is a carbon atom;
R'$_5$ borne by the quaternized nitrogen atom, in the case of W$_3$, is a bond to LK;
R'$_7$ is chosen from optionally substituted C$_1$-C$_4$ alkyl radicals; optionally substituted phenyl radicals; and optionally substituted benzyl radicals;
the bond c links the cationic radical chosen from those of formulae (1) to (11) to the azo group; the bond may be on the main or secondary ring; for example, the bond a with the azo group is on the main ring;
p is an integer ranging from 0 to 4, p' is an integer ranging from 0 to 2, and p" is an integer ranging from 0 to 3; with the proviso that when the main ring does not bear the maximum number of substituents, then the unsubstituted position(s) bear(s) a nitrogen atom;
LK is chosen from saturated and unsaturated, linear and branched, cyclic and non-cyclic, aromatic and non-aromatic, optionally substituted C$_2$-C$_{40}$, such as C$_2$-C$_{20}$, hydrocarbon-based chains, optionally interrupted with at least one hetero atom or group comprising at least one hetero atom, such as oxygen or nitrogen; wherein the group LK does not comprise a peroxo, nitro or nitroso group or bond; if LK is linked to $W'_5$, LK may end with a hetero atom or group comprising at least one hetero atom, such as oxygen or nitrogen; if LK is linked to $W_6$, LK may end with a group comprising at least one hetero atom chosen from —CO— and —SO$_2$—; if LK is linked to $W_3$, the bonding takes place via a carbon atom; and the electrical neutrality of the compounds of formula (I) is ensured by at least one cosmetically acceptable anion An.

The present disclosure also relates to dye compositions comprising, in a medium that is suitable for dyeing keratin fibers, at least one direct dye chosen from the compounds of formula (I) and the acid addition salts thereof, as described above.

The present disclosure still further relates to a process for dyeing keratin fibers comprising applying the compositions disclosed herein to wet or dry fibers, for a period of time that is sufficient to obtain the desired effect.

Finally, the present disclosure relates to a multi-compartment device comprising, in at least one first compartment, at least one composition as disclosed herein, and, in at least one second compartment, at least one oxidizing composition.

It has been found that the compounds of formula (I) show good color-fastness with respect to external agents such as, for example, shampoos, even when the keratin fiber is sensitized. Furthermore, the compounds, which are dissymmetrical compounds, allow access to colorations that are less chromatic than those obtained with symmetrical compounds.

Other characteristics and benefits of the present disclosure will emerge more clearly upon reading the description and the examples presented.

In the text herein below, unless otherwise indicated, the limits delimiting a range of values are included in that range.

Moreover, the keratin fibers forming the subject of the treatment according, to the invention can be human keratin fibers, such as the hair.

For the purposes of the present invention, and unless otherwise indicated:
  an alkyl radical is linear or branched,
  an alkyl radical or the alkyl part of a radical is said to be substituted when it comprises at least one substituent chosen from:
    hydroxyl groups,
    $C_1$-$C_4$ alkoxy groups,
    $C_2$-$C_4$ (poly)hydroxyalkoxy groups,
    amino groups,
    amino groups substituted with at least one $C_1$-$C_4$ alkyl group, which may be identical or different, optionally bearing at least one hydroxyl group, the alkyl radicals possibly forming, with the nitrogen to which they are attached, a 5- or 6-membered heterocycle optionally comprising at least one other nitrogen or non-nitrogen hetero atom;
  an aryl or heteroaryl radical or the aryl or heteroaryl part of a radical is said to be substituted when it comprises at least one substituent borne by a carbon atom, chosen from
    $C_1$-$C_{16}$, such as $C_1$-$C_8$, alkyl radicals, optionally substituted with at least one radical chosen from hydroxyl, $C_1$-$C_2$ alkoxy, $C_2$-$C_4$ (poly)hydroxyalkoxy, and acylamino radicals, and amino radicals substituted with two identical or different $C_1$-$C_4$ alkyl radicals, optionally bearing at least one hydroxyl group, or the two radicals possibly forming, with the nitrogen atom to which they are attached, a 5- to 7-membered, for instance a 5- or 6-membered heterocycle, optionally comprising another nitrogen or non-nitrogen hetero atom;
    halogen atoms, such as chlorine, fluorine or bromine;
    hydroxyl groups;
    $C_1$-$C_2$ alkoxy radicals;
    $C_2$-$C_4$ (poly)hydroxyalkoxy radicals;
    amino radicals;
    amino radicals substituted with one or two identical or different $C_1$-$C_4$ alkyl radicals optionally bearing at least one hydroxyl group, or amino radicals with two optionally substituted $C_1$-$C_2$ alkyl radicals;
    acylamino radicals (—NR—COR') in which the radical R is chosen from a hydrogen atom and $C_1$-$C_4$ alkyl radicals optionally bearing at least one hydroxyl group and the radical R' is a $C_1$-$C_2$ alkyl radical;
    carbamoyl radicals ((R)$_2$N—CO—) in which the radicals R, which may be identical or different, are chosen from hydrogen atoms and $C_1$-$C_4$ alkyl radicals optionally bearing at least one hydroxyl group;
    alkylsulfonylamino radicals (R'SO$_2$—NR—) in which the radical R is chosen from a hydrogen atom and $C_1$-$C_4$ alkyl radicals optionally bearing at least one hydroxyl group and the radical R' is chosen from $C_1$-$C_4$ alkyl radicals and phenyl radicals;
    aminosulfonyl radicals ((R)$_2$N—SO$_2$—) in which the radicals R, which may be identical or different, are chosen from hydrogen atoms and $C_1$-$C_4$ alkyl radicals optionally bearing at least one hydroxyl group,
  the cyclic or heterocyclic part of a non-aromatic radical is said to be substituted when it comprises at least one substituent borne by a carbon atom, chosen from:
    hydroxyl groups,
    $C_1$-$C_4$ alkoxy groups,
    $C_2$-$C_4$ (poly)hydroxyalkoxy groups,
    alkylcarbonylamino((RCO—NR'—) groups in which the radical R' is chosen from a hydrogen atom and $C_1$-$C_4$ alkyl radicals optionally bearing at least one hydroxyl group and the radical R is chosen from $C_1$-$C_2$ alkyl radicals,
    amino radicals substituted with two identical or different $C_1$-$C_4$ alkyl groups optionally bearing at least one hydroxyl group, the two alkyl radicals possibly forming, with the nitrogen atom to which they are attached, a 5- or 6-membered heterocycle optionally comprising at least one other nitrogen or non-nitrogen hetero atom.

As indicated previously, the present disclosure relates to compounds chosen from the abovementioned formula (I).

For example, the compound of formula (I), Dye1-LK-Dye2, can be such that the radicals $R_1$, $R_2$, $R_3$ and $R'_1$, which may be identical or different, are chosen from:
  hydrogen atoms;
  optionally substituted $C_1$-$C_6$ alkyl radicals;
  aryl and arylalkyl radicals, such as phenyl or benzyl, the aryl part being optionally substituted;
  wherein the radicals $R_1$, $R_2$ or $R_3$ of $W'_6$, independently of each other, can optionally form, with part of the group LK and with the nitrogen or oxygen atom to which each is attached, a saturated or unsaturated, aromatic or non-aromatic, optionally substituted 5- to 7-membered heterocycle; and
  wherein the radical $R'_1$ of $W_6$ may optionally form, with the nitrogen atom to which it is attached and a part of the group LK, a saturated or unsaturated, aromatic or non-aromatic, optionally substituted 5-, 6- or 7-membered heterocycle optionally comprising another hetero atom chosen from nitrogen and oxygen.

As a further example, according to one embodiment of the present disclosure, the radicals $R_1$, $R_2$, $R_3$ and $R'_1$, which may be identical or different, are chosen from:

hydrogen atoms;

optionally substituted $C_1$-$C_3$ alkyl radicals, such as methyl, ethyl, 2-hydroxyethyl or 2-methoxyethyl;

phenyl radicals, optionally substituted with at least one radical chosen from hydroxyl, $C_1$-$C_2$ alkoxy and amino radicals, and amino radicals substituted with at least one $C_1$-$C_4$ group optionally bearing at least one hydroxyl group;

wherein the radical R' of $W_6$ can form, with the nitrogen atom to which it is attached and part of the group LK, a 5- or 6-membered heterocycle of pyrrolidine, piperidine, piperazine or homopiperazine type optionally substituted with at least one methyl, hydroxyl, amino or (di)methylamino radical.

According to another embodiment of the present disclosure, for instance, the radicals $R_1$, $R_2$, $R_3$ and $R'_1$, which may be identical or different, are chosen from:

hydrogen atoms;

methyl, ethyl and 2-hydroxyethyl radicals;

phenyl radicals, optionally substituted with a hydroxyl, methoxy, amino, (di)methylamino or (di)(2-hydroxyethyl)amino radical;

wherein the radical $R'_1$ of $W_6$ can form, with the nitrogen atom to which it is attached and part of the group LK, a 5- to 7-membered heterocycle such as pyrrolidine, 3-hydroxypyrrolidine, 3-dimethylaminopyrrolidine, piperidine, 2-(2-hydroxyethylpiperidine), 4-(aminoethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine or 1-methyl-1,4-perhydrodiazepine.

For example, with respect to the radicals $R_4$, $R_5$, $R_6$, $R'_6$, $R_7$, $R_8$, $R_{10}$ and $R_{11}$, these radicals, which may be identical or different, may be chosen from:

hydrogen atoms for $R_4$, $R_5$, $R_7$, $R_8$, $R_{10}$ and $R_{11}$;

optionally substituted $C_1$-$C_{16}$, such as $C_1$-$C_8$, alkyl radicals;

halogen atoms such as chlorine, fluorine or bromine;

hydroxyl groups;

$C_1$-$C_2$ alkoxy radicals;

$C_2$-$C_4$ (poly)hydroxyalkoxy radicals;

amino radicals;

amino radicals substituted with one or two $C_1$-$C_4$ alkyl radicals, which may be identical or different, optionally bearing at least one hydroxyl or $C_1$-$C_4$ dialkylamino group;

alkylcarbonylamino radicals (RCO—NR'—) in which the radical R is chosen from $C_1$-$C_4$ alkyl radicals and the radical R' is chosen from a hydrogen atom and $C_1$-$C_4$ alkyl radicals;

carbamoyl radicals ($(R)_2$N—CO—) in which the radicals R, which may be identical or different, are chosen from hydrogen atoms and $C_1$-$C_4$ alkyl radicals optionally bearing at least one hydroxyl group;

alkylsulfonylamino radicals (R'SO$_2$—NR—) in which the radical R is chosen from a hydrogen atom and $C_1$-$C_4$ alkyl radicals optionally bearing at least one hydroxyl group, the radical R' is chosen from $C_1$-$C_4$ alkyl radicals;

aminosulfonyl radicals ($(R)_2$N—SO$_2$—) in which the radicals R, which may be identical or different, are chosen from hydrogen atoms and $C_1$-$C_4$ alkyl radicals optionally bearing at least one hydroxyl group; and a bond from W'5 to W'6.

For further example, the radicals $R_4$, $R_5$, $R_6$, $R'_6$, $R_7$, $R_8$, $R_{10}$ and $R_{11}$, which may be identical or different, may be chosen from:

hydrogen atoms for $R_4$, $R_5$, $R_6$, $R'_6$, $R_7$, $R_8$, $R_{10}$ and $R_{11}$;

$C_1$-$C_4$ alkyl radicals optionally substituted with at least one radical chosen from hydroxyl and acylamino radicals, and amino radicals substituted with two identical or different $C_1$-$C_2$ alkyl radicals, optionally bearing at least one hydroxyl group, or a $C_1$-$C_2$ alkoxy radical;

amino radicals;

amino radicals substituted with one or two identical or different $C_1$-$C_2$ alkyl radicals, optionally bearing at least one hydroxyl group;

acylamino radicals;

carbamoyl radicals;

sulfonylamino radicals;

hydroxyl radicals;

$C_1$-$C_2$ alkoxy radicals; and a bond from $W'_5$ to $W'_6$.

According to another embodiment of the present disclosure, the radicals $R_4$, $R_5$, $R_6$, $R'_6$, $R_7$, $R_8$, $R_{10}$ and $R_{11}$, which may be identical or different, can be chosen from:

hydrogen atoms for $R_4$, $R_5$, $R_6$, $R'_6$, $R_7$, $R_8$, $R_{10}$ and $R_{11}$;

methyl, ethyl, propyl, 2-hydroxyethyl, methoxy, ethoxy, 2-hydroxyethyloxy, 3-hydroxypropyloxy and 2-methoxyethyl radicals;

sulfonylamino radicals; amino, methylamino, dimethylamino, 2-hydroxyethylamino, 3-hydroxypropylamino and acylamino radicals; hydroxyl radicals;

chlorine atoms; and a bond from $W'_5$ to $W'_6$.

The radical $R_9$, may be chosen from a hydrogen atom, $C_1$-$C_{15}$ alkyl radicals; $C_2$-$C_6$ monohydroxyalkyl radicals; $C_2$-$C_6$-polyhydroxyalkyl radicals; $(C_1$-$C_6)$alkoxy$(C_2$-$C_6)$ alkyl radicals; optionally substituted aryl radicals, such as phenyl; optionally substituted arylalkyl radicals, such as benzyl; $C_2$-$C_6$ amidoalkyl radicals; $C_2$-$C_6$ aminoalkyl radicals, the amine of which is substituted with two identical or different, optionally substituted $C_1$-$C_4$ alkyl radicals. In addition, the radical $R_9$ may be such that the atom directly linked to the nitrogen atom is a carbon atom.

For example, $R_9$ may be chosen from a hydrogen atom, $C_1$-$C_6$ alkyl radicals; $C_2$-$C_6$ monohydroxyalkyl radicals; $C_2$-$C_6$ polyhydroxyalkyl radicals; $(C_1$-$C_6)$alkoxy$(C_2$-$C_6)$ alkyl radicals; phenyl radicals optionally substituted with at least one entity chosen from chlorine atoms, hydroxyl groups, RCO—NH— groups in which R is chosen from $C_1$-$C_4$ alkyl radicals or an amino radical substituted with two identical or different $C_1$-$C_4$ alkyl radicals; benzyl radicals; $C_1$-$C_6$ aminoalkyl radicals; $C_1$-$C_6$ aminoalkyl radicals in which the amine is substituted with two identical or different $C_1$-$C_4$ alkyl radicals. Furthermore, the radical $R_9$ may be such that the atom directly linked to the nitrogen atom is a carbon atom.

According to one embodiment of the present disclosure, $W_2$, $W_5$ and $W'_5$, which may be identical or different, are chosen from the groups of formula (a) or (c).

According to this embodiment, $X_1$ may be a group $CR_7$. Further according to this embodiment, $X_2$ may be a group CR$_8$, R$_4$, R$_5$, R$_6$, R'$_6$, R$_7$ and R$_8$, which may be identical or different, have the same meanings as above.

With respect to the groups W$_3$ and W$_4$, these groups, which may be identical or different, may be a heterocycle chosen from those of formulae (1), (2), and (3):

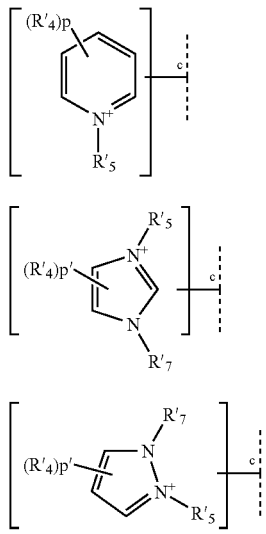

wherein R'$_4$, R'$_5$, R'$_7$, p, p' and a are defined as above.

For example, R'$_5$ and R'$_7$ can have the same definitions as R$_9$, with the exception of hydrogen.

According to one embodiment of the present disclosure, the groups W$_3$ and W$_4$ are cationic aromatic heterocyclic groups chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium.

According to another embodiment of the present disclosure, the groups W$_3$ and W$_4$, which may be identical or different, may be cationic aromatic heterocycles chosen from 2-imidazolium, 2-pyridinium, 3-pyridinium, 4-pyridinium, 2-quinolinium, 4-quinolinium, 3-pyrazolium, 4-pyrazolium, 3-indazolium, 4-indazolium and 7-indazolium.

In the case of W$_3$, the cationic heterocyclic radicals may be attached to the group LK via a quaternized nitrogen atom, i.e., via R'$_5$.

In formula (I), LK does not bear a cationic charge.

In one embodiment of the present disclosure, for example, LK may be chosen from linear, branched and cyclic, aromatic and non-aromatic C$_2$-C$_{20}$ alkyl chains:
- optionally interrupted with at least one hetero atom and/or group comprising at least one hetero atom, for instance —O—, —NR'—, —CO— or —SO$_2$—, on condition that there are no nitro, nitroso or peroxo groups or bonds in the group LK;
- optionally ending with a hetero atom or group bearing at least one hetero atom, such as oxygen or nitrogen, if LK is linked to W'$_5$;
- optionally ending with a group bearing at least one hetero atom chosen from —CO— and —SO$_2$— if LK is linked to W$_6$;
- if LK is linked to W$_3$ via a quaternized nitrogen atom, LK is directly linked to W$_3$ via a carbon atom; in other words, LK cannot end with a hetero atom or a group comprising at least one hetero atom if LK is linked to W$_3$ via a quaternized nitrogen atom;
- optionally substituted with at least one radical chosen from hydroxyl, C$_1$-C$_2$ alkoxy, C$_2$-C$_4$ (poly)hydroxyalkoxy, amino substituted with at least one linear or branched C$_1$-C$_2$ alkyl group optionally bearing at least one hydroxyl group.

For instance, LK may be chosen from linear and branched C$_2$-C$_{20}$ alkyl chains optionally substituted with hydroxyl, amino substituted with several linear or branched C$_1$-C$_4$ alkyl groups optionally bearing at least one hydroxyl group. Furthermore, when LK is linked to W'$_5$, LK may optionally end with at least one hetero atom or group comprising at least one hetero atom, for instance —O—, —NR'—, —CO— or —SO$_2$—.

According to another embodiment of the present disclosure, LK may be chosen from linear and branched C$_2$-C$_8$ alkyl chains, optionally substituted with at least one radical chosen from hydroxyl, C$_1$-C$_2$ alkoxy and C$_1$-C$_2$ (di)alkylamino radicals, with a heterocycle. Furthermore, when LK is linked to W'$_5$, LK may optionally end with at least one hetero atom or group comprising at least one hetero atom, for instance —O—, —NR'—, —CO— or —SO$_2$—.

An is an organic or mineral anion or mixture of anions, so as to respect the electrical neutrality of the compound, chosen, for example, from halides such as chlorides, bromides, fluorides or iodides; hydroxides; sulfates; hydrogen sulfates; (C$_1$-C$_6$)alkyl sulfates, for instance methyl sulfate or ethyl sulfate; phosphates; carbonates; hydrogen carbonates; perchlorates; acetates; tartrates; citrates; oxalates; (C$_1$-C$_6$) alkylsulfonates such as methylsulfonate; arylsulfonates, which are unsubstituted or substituted with a C$_1$-C$_4$ alkyl radical, for instance a 4-tolylsulfonate.

The acid addition salts of the compounds of formula (I) may be, for example, halides, for instance chlorides or bromides, sulfates, alkyl sulfates for which the linear or branched alkyl part is of C$_1$-C$_6$, for instance methosulfate or ethosulfate ions, hydrogen carbonates, perchlorates, carboxylic acid salts, for instance acetates; citrates; tartrates, alone or in combination.

In accordance with one embodiment of the present disclosure, the compounds chosen from those of formula (I) are chosen from those of formulae:

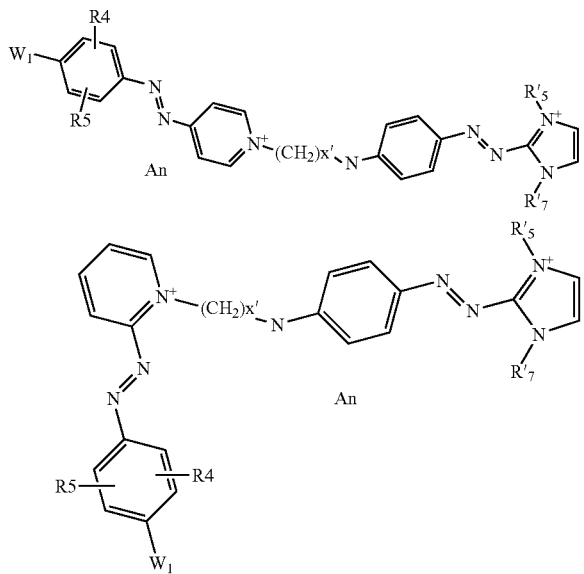

-continued

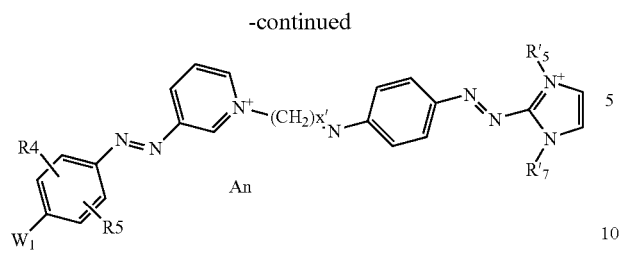

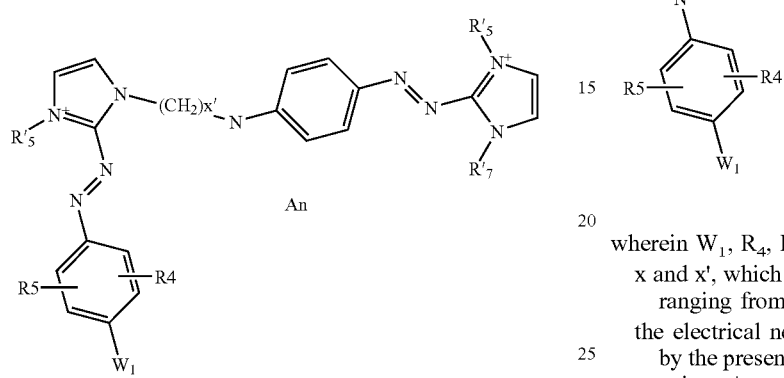

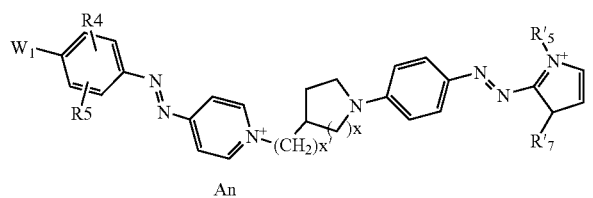

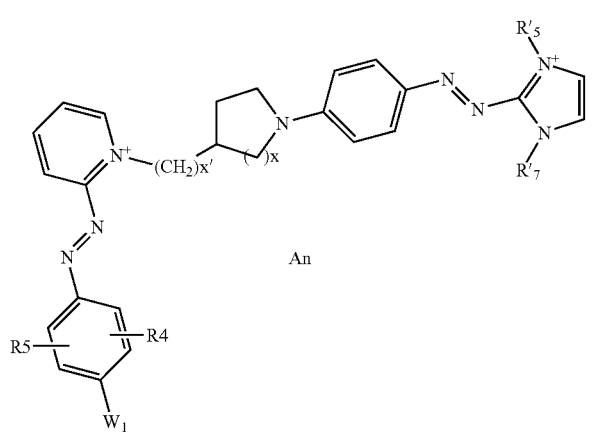

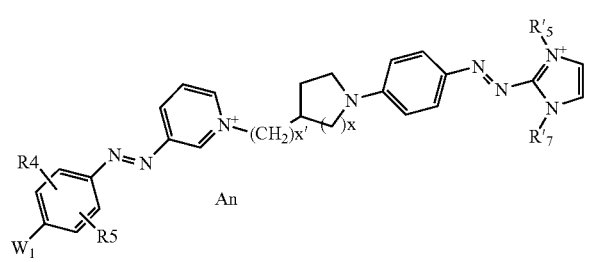

-continued

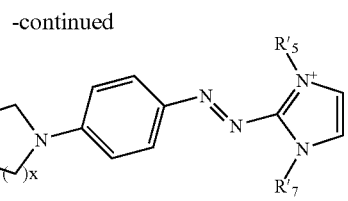

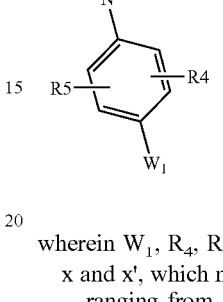

wherein $W_1$, $R_4$, $R_5$, $R'_5$ and $R'_7$ are as defined above;

x and x', which may be identical or different, are integers ranging from 1 to 10, such as from 1 to 6;

the electrical neutrality of the molecule being respected by the presence of one or more cosmetically acceptable anions An as defined above.

These compounds can be obtained from preparation processes described, for example, in U.S. Pat. No. 5,708,151; *J. Chem. Res.*, Synop. (1998), (10), 648-649; U.S. Pat. Nos. 3,151,106, and 5,852,179, *Heterocycles*, 1987, 26 (2) 313-317; *Synth. Commun.* 1999, 29 (13), 2271-2276; and *Tetrahedron*, 1983, 39 (7), 1091-1101.

The present disclosure also relates to a composition comprising, in a medium that is suitable for dyeing keratin fibers, at least one direct dye chosen from those of formula (I) and the acid addition salts thereof.

The at least one compound of formula (I), or each of the compounds of formula (I), can be present in the composition in an amount ranging from 0.001% to 20% by weight, for instance from 0.01% to 10% by weight, such as from 0.05% to 5% by weight, relative to the total weight of the dye composition.

The composition according to the invention may also comprise at least one oxidation base. The at least one oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines that may be used as disclosed herein, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bis(phenyl)alkylenediamines that may be used as disclosed herein, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamin, 1,8-bis(2,5-diaminophenoxy)-3,6-dioxaoctane, and the acid addition salts thereof.

Among the para-aminophenols that may be used as disclosed herein, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols that may be used as disclosed herein, non-limiting mention may be made of, for example, 2-aminophenol, 2-amino-5-methylphenol, 2-amino-6-methylphenol and 5-acetamido-2-aminophenol, and the acid addition salts thereof.

Among the heterocyclic bases that may be used as disclosed herein, non-limiting mention may be made of, for example, pyridine derivatives, pyrimidine derivatives and pyrazole derivatives.

Non-limiting examples of pyridine derivatives that may be mentioned include the compounds described, for instance, in British Patent Nos. GB 1 026 978 and GB 1 153 196, and 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Non-limiting examples of pyrimidine derivatives that can be mentioned include the compounds described, for example, in German Patent No. DE 2 359 399; Japanese Patent Nos. JP 88-169 571 and JP 05-163 124; European Patent No. EP 0 770 375, or International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Non-limiting examples of the pyrazole derivatives that may be mentioned include the compounds described in German Patent Nos. DE 3 843 892 and DE 4 133 957, and International Patent Application Nos. WO 94/08969 and WO 94/08970, French Patent Application No. FR-A-2 733 749, and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The composition according to the present disclosure may also comprise at least one coupler conventionally used for dyeing keratin fibers. Among these couplers, non-limiting mention may be made of meta-phenylenediamines, meta-aminophenols, meta-diphenols, naphthalene-based couplers and heterocyclic couplers. Non-limiting examples of couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxyethylamino)toluene and the acid addition salts thereof.

In the composition of the present disclosure, the at least one coupler can be present in an amount ranging from 0.001% to 10% by weight, for instance from 0.005% to 6% by weight, relative to the total weight of the dye composition. The at least one oxidation base can be present in an amount ranging for example, from 0.001% to 10% by weight, such as from 0.005% to 6% by weight, relative to the total weight of the dye composition.

In general, the addition salts with an acid that may be used in the context of the dye compositions of the present disclosure for the oxidation bases and couplers can be chosen from, for example, the hydrochlorides, hydrobromides, sulfates, citrates, succinates, tartrates, lactates, tosylates, benzenesulfonates, phosphates and acetates.

The composition according to the present disclosure may optionally comprise at least one additional direct dye other than the compounds of formula (I). This optional additional direct dye may be chosen from cationic and nonionic species.

Non-limiting examples of such direct dyes that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

The optional additional direct dye may be chosen, by way of non-limiting example, from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one optional additional direct dye may also be chosen from yellow and green-yellow nitrobenzene direct dyes; non-limiting mention may be made, for example, of the compounds chosen from:
1-(β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Non-limiting mention may also be made of blue or violet nitrobenzene direct dyes, for instance:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines of the formula:

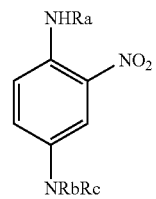

wherein:
$R_b$ is chosen from $C_1$-$C_4$ alkyl radicals and β-hydroxyethyl, β-hydroxypropyl and γ-hydroxypropyl radicals;
$R_a$ and $R_c$, which may be identical or different, are chosen from β-hydroxyethyl, β-hydroxypropyl, γ-hydroxypropyl and β,γ-dihydroxypropyl radicals, wherein at least one of the radicals $R_b$, $R_c$ or $R_a$ is a γ-hydroxypropyl radical and $R_b$ and $R_c$ not simultaneously being able to denote a β-hydroxyethyl radical when $R_b$ is a γ-hydroxypropyl radical, such as those described in French Patent No. FR 2 692 572.

Among the azo direct dyes that may be used according to the present disclosure, non-limiting mention may be made of the cationic azo dyes described in International Patent Application Nos. WO 95/15144 and WO 95/01772, and European Patent Application No. EP 714 954.

Among these compounds, mention may be made, by way of non-limiting example, of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Non-limiting examples of the azo direct dyes that may also be mentioned include the following dyes described in the Color Index International 3rd edition:
Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23, Acid Orange 24, and Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Non-limiting examples of the quinone direct dyes that may be mentioned include the following dyes:

Disperse Red 15,

Solvent Violet 13,

Acid Violet 43,

Disperse Violet 1,

Disperse Violet 4,

Disperse Blue 1,

Disperse Violet 8,

Disperse Blue 3,

Disperse Red 11,

Acid Blue 62,

Disperse Blue 7,

Basic Blue 22,

Disperse Violet 15, and

Basic Blue 99;

and also the following compounds:

1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, and 1,4-bis(β,γ-dihydroxypropylamino)anthraquinone.

Non-limiting examples of the azine dyes that may be mentioned include:

Basic Blue 17 and Basic Red 2.

Among the triarylmethane dyes that may be used according to the present disclosure, non-limiting mention may be made of the following compounds:

Basic Green 1,

Acid Blue 9,

Basic Violet 3,

Basic Violet 14,

Basic Blue 7,

Acid Violet 49,

Basic Blue 26, and

Acid Blue 7.

Among the indoamine dyes that may be used according to the present disclosure, non-limiting mention may be made of:

2-β-hydroxyethylamino-5-[bis(β-4'-hydroxyethyl)amino]anilino-1,4-benzoquinone;

2-β-hydroxyethylamino-5-(2'-methoxy-4'-amino)anilino-1,4-benzoquinone;

3-N(2'-chloro-4'-hydroxy)phenylacetylamino-6-methoxy-1,4-benzoquinoneimine;

3-N(3'-chloro-4'-methylamino)phenylureido-6-methyl-1,4-benzoquinoneimine; and

3-[4'-N-(ethylcarbamylmethyl)amino]phenylureido-6-methyl-1,4-benzoquinoneimine.

Among the dyes of tetraazapentamethine type that may be used according to the present disclosure, non-limiting mention may be made of the compounds given in the table below, An being defined as above:

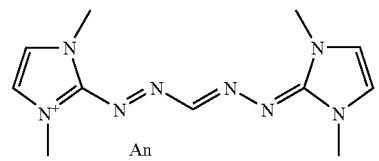

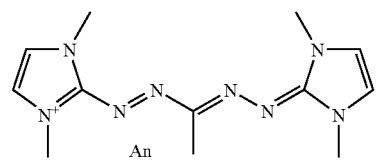

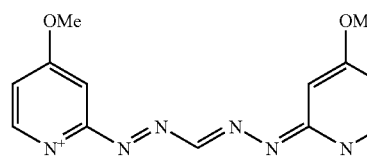

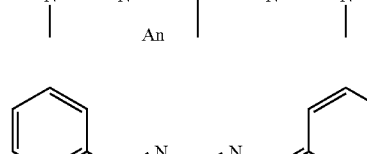

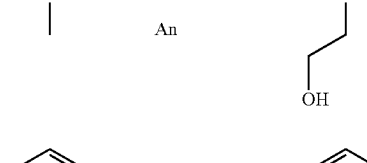

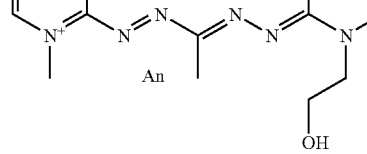

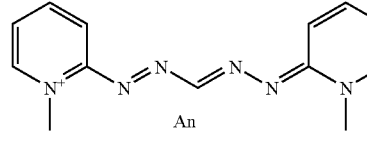

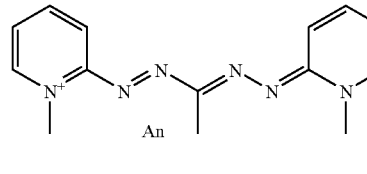

-continued

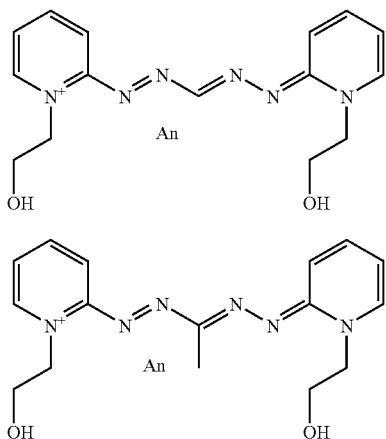

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Extracts or decoctions comprising these natural dyes may also be used, such as henna-based poultices or extracts.

When present, the at least one additional direct dye can be present in the composition in an amount ranging from 0.001% to 20% by weight, relative to the weight of the composition, for instance, from 0.01% to 10% by weight, relative to the weight of the composition.

The medium that is suitable for dyeing, also known as the dye support, generally comprises water, or comprises a mixture of water and at least one organic solvent to dissolve the compounds that are not sufficiently water-soluble.

For example, the at least one organic solvent is chosen from linear and branched, for instance saturated monoalcohols and diols comprising from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ether, propylene glycol and its ethers, for instance propylene glycol monomethyl ether, butylene glycol and dipropylene glycol; and also diethylene glycol alkyl ethers, such as of $C_1$-$C_4$, for instance diethylene glycol monoethyl ether or monobutyl ether, alone or as a mixture.

The usual solvents described above, when they are present, can be present in an amount ranging from 1% to 40% by weight, such as from 5% to 30% by weight, relative to the total weight of the composition.

The dye composition in accordance with the present disclosure may also comprise at least one adjuvant chosen from the various adjuvants conventionally used in compositions for dyeing the hair, such as anionic, cationic, nonionic, amphoteric or zwitterionic surfactants or mixtures thereof; anionic, cationic, nonionic, amphoteric or zwitterionic polymers or mixtures thereof; mineral or organic thickeners, for instance anionic, cationic, nonionic and amphoteric associative polymeric thickeners; antioxidants; penetrating agents; sequestering agents; fragrances; buffers; dispersants; conditioning agents, for instance silicones, which may or may not be volatile or modified; film-forming agents; ceramides; preserving agents; and opacifiers.

The at least one adjuvant, when present, can be present in an amount, for each adjuvant, ranging from 0.01% to 20% by weight, relative to the weight of the composition.

Needless to say, a person skilled in the art will take care to select this or these optional additional compounds such that the beneficial properties intrinsically associated with the oxidation dye composition in accordance with the present disclosure are not, or are not substantially, adversely affected by the envisaged addition(s).

The pH of the dye composition in accordance with the present disclosure can range from 3 to 12, for instance from 5 to 11. It may be adjusted to the desired value using acidifying or basifying agents usually used in the dyeing of keratin fibers, or alternatively using standard buffer systems.

Among the acidifying agents that may be used, non-limiting mention may be made of, for example, mineral or organic acids such as hydrochloric acid, orthophosphoric acid, sulfuric acid, carboxylic acids such as acetic acid, tartaric acid, citric acid and lactic acid, and sulfonic acids.

Among the basifying agents that may be used, non-limiting mention may be made of, for example, aqueous ammonia, alkaline carbonates, alkanolamines such as monoethanolamine, diethanolamine and triethanolamine and derivatives thereof, sodium hydroxide, potassium hydroxide and the compounds having the following formula:

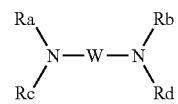

wherein W is a propylene residue optionally substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals, and $C_1$-$C_4$ hydroxyalkyl radicals.

The dye composition according to the present disclosure may be in various forms, such as in the form of liquids, creams or gels, or in any other form that is suitable for dyeing keratin fibers, such as human hair.

The composition according to the present disclosure may also comprise at least one oxidizing agent. In this case, the composition is referred to as a ready-to-use composition.

As used herein, the term "ready-to-use composition" is understood to mean a composition intended to be applied immediately to the keratin fibers, i.e. it may be stored in unmodified form before use or may result from the extemporaneous mixing of two or more compositions. The ready-to-use composition may also be obtained by mixing the composition according to the present disclosure with an oxidizing composition, which comprises at least one oxidizing agent.

The at least one optional oxidizing agent used to make the read-to-use composition may be any oxidizing agent conventionally used in the field. Thus, it may be chosen from hydrogen peroxide, urea peroxide, alkali metal bromates, persalts such as perborates and persulfates, and also enzymes, among which non-limiting mention may be made of peroxidases, 2-electron oxidoreductases such as uricases, and 4-electron oxygenases, for instance laccases. In one embodiment of the present disclosure, hydrogen peroxide is used.

The at least one oxidizing agent, when present, can be present in an amount ranging from 1% to 40% by weight, relative to the weight of the ready-to-use composition, for instance from 1% to 20% by weight, relative to the weight of the ready-to-use composition.

The oxidizing composition used can be an aqueous composition and may be in the form of a solution or an emulsion.

The composition free of oxidizing agent can be mixed with about 0.5 to 10 weight equivalents of the oxidizing composition before use or simultaneous with use, to make the ready-to-use composition.

The pH of the ready-to-use composition can range from 4 to 12, such as from 7 to 11.5.

The pH of the composition may be adjusted using an acidifying or basifying agent chosen for example, from those mentioned previously in the context of the description according to the present disclosure.

The present disclosure also relates to a dyeing process that comprises the application of a dye composition as disclosed herein to wet or dry keratin fibers.

The application to the fibers of the dye composition comprising the at least one direct dye chosen from the compounds of formula (I) and the acid addition salts thereof, optionally at least one oxidation base optionally combined with at least one coupler, and optionally at least one additional direct dye, may be performed in the presence of an oxidizing agent.

This optional oxidizing agent may be added to the composition comprising the at least one compound of formula (I) and the optional oxidation bases, couplers and/or additional direct dyes, either at the time of use, or directly onto the keratin fiber.

The oxidizing composition may also comprise at least one adjuvant chosen from various adjuvants conventionally used in compositions for dyeing the hair and as defined above.

The pH of the oxidizing composition comprising the oxidizing agent is such that, after mixing with the dye composition, the pH of the resulting composition applied to the keratin fibers ranges from 4 to 12, for instance ranging from 7 to 11.5. It may be adjusted to the desired value by means of acidifying or basifying agents usually used in the dyeing of keratin fibers and as defined above.

The composition that is finally applied to the keratin fibers may be in various forms, such as in the form of liquids, creams or gels or in any other form that is suitable for dyeing keratin fibers, such as human hair.

According to one embodiment, the composition according to the present disclosure is free of oxidation base and of coupler.

The composition applied may optionally comprise at least one oxidizing agent.

The composition is thus applied to the wet or dry keratin fibers and is then left for a period of leave-in time that is sufficient to obtain the desired coloration.

Whatever embodiment adopted (with or without oxidizing agent), the leave-in time can range from a few seconds to one hour, for instance from 3 minutes to 30 minutes.

The temperature at which the composition is left to act can range from 15° C. to 220° C., for instance from 15° C. to 80° C., such as from 15° C. to 40° C.

After the leave-in time, the composition is removed by rinsing with water, optionally followed by washing with a shampoo, and then optionally drying.

The present disclosure also relates to a multi-compartment device or dyeing "kit" comprising at least one first compartment comprising at least one dye composition as disclosed herein, and at least one second compartment comprising at least one oxidizing composition. This device may be equipped with an applicator for applying the desired mixture to the hair, such as the devices described in French Patent No. FR 2 586 913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The examples that follow serve to illustrate the invention without, however, being limiting in nature.

EXAMPLES

Examples 1-4

Synthesis of the Following Dye Compounds

Example 1 (compound 5)

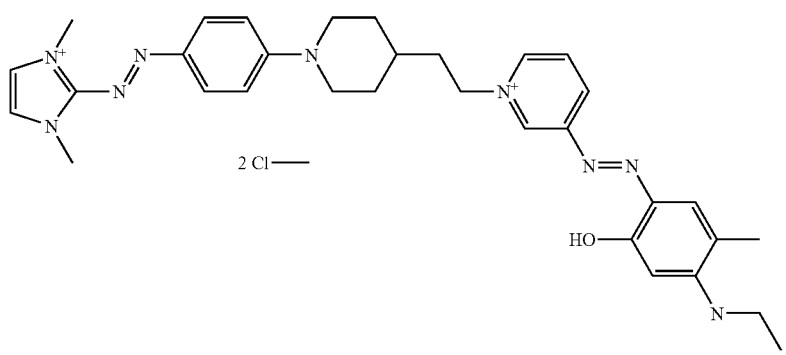

-continued
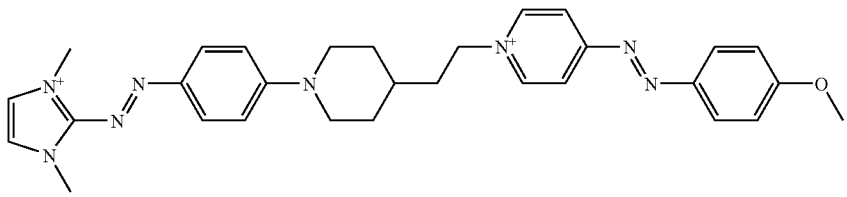
Example 2 (compound 7)
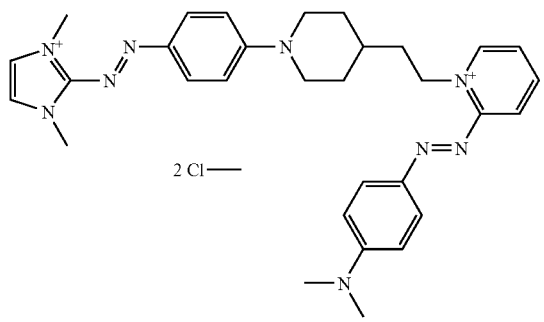
Example 3 (compound 9)
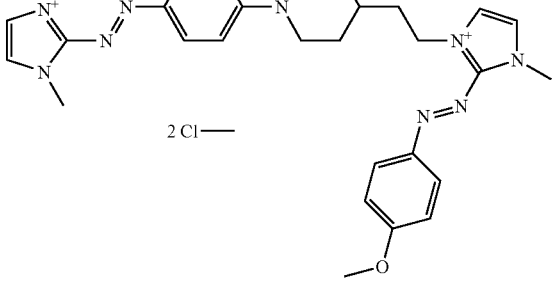
Example 4 (compound 11)
These compounds were obtained in the following manner:
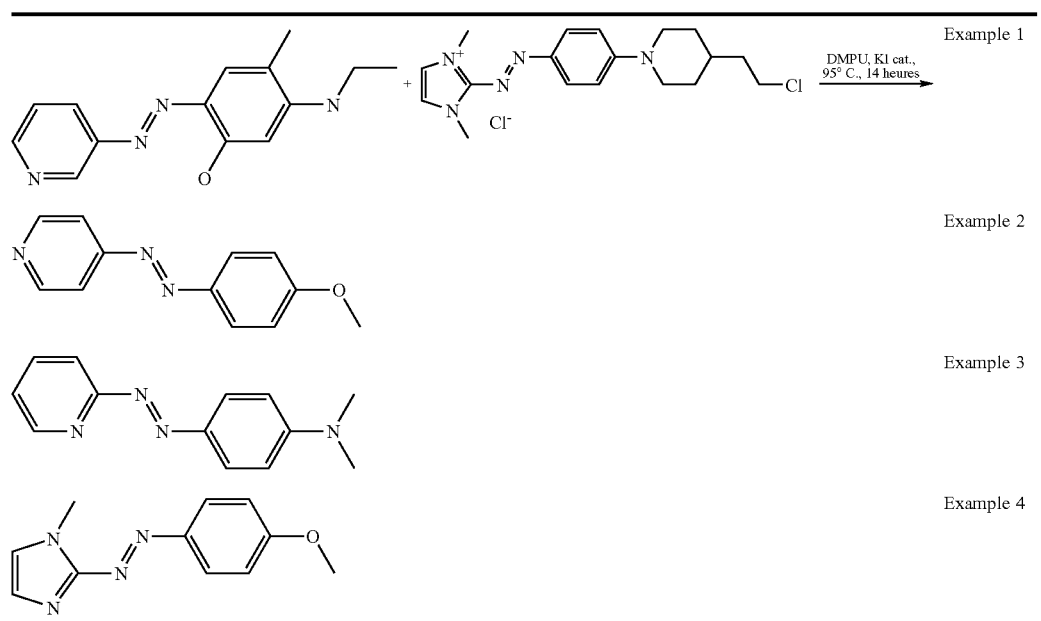
Example 1a
Synthesis of the Halogenated Derivative (Compound 3) Used in the Synthesis of Example 1
The halogenated derivative (compound 3) was prepared in the following manner:
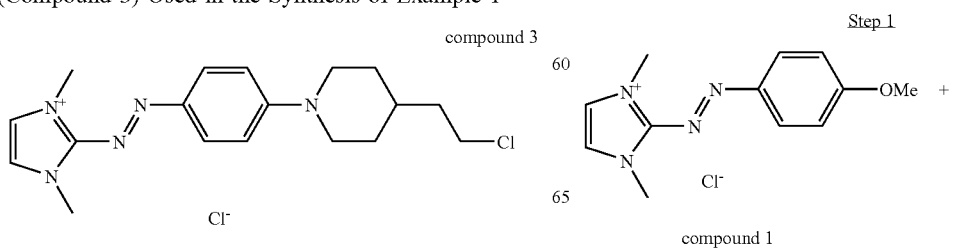

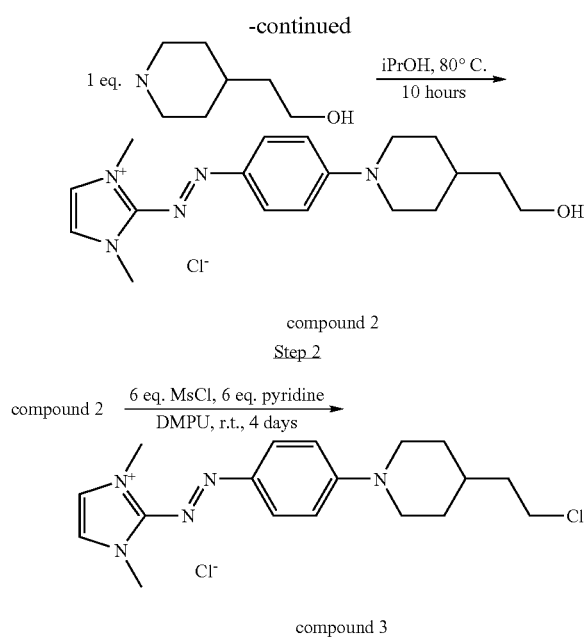

(Compound 1 was synthesized according to the synthesis disclosed in U.S. Pat. No. 5,708,151.)

Procedure for Synthesis of the Halogenated Derivative (Compound 3)

Step 1

Compound 1 (10 g) was placed in 50 ml of isopropanol in a three-necked flask with stirring; the amine (4.85 g; 1 eq.), predissolved in 20 ml of isopropanol, was then added to the reaction medium. The mixture was heated to 80° C. (external temperature) with stirring.

After 10 hours, the heating was stopped and the mixture was allowed to cool to room temperature.

After precipitating the product from an acetone/ethyl acetate mixture (100 ml/400 ml) followed by filtration, 10.83 g of a red-violet solid were recovered.

The NMR and mass spectra were in accordance with compound 2.

Step 2

Compound 2 (1 g), 1,3-dimethyl-3,4,5,6-tetrahydro-2 (1H)-pyrimidinone (20 ml), methanesulfonyl chloride (1.27 ml, 6 eq.) and pyridine (1.3 g, 6 eq.) were placed in a three-necked flask.

The mixture was stirred at room temperature for 4 days.

The product was precipitated from ethyl acetate and then filtered off. The precipitate was dissolved in water and then extracted with dichloromethane. The organic phase was dried over sodium sulfate, filtered and then concentrated.

Compound 3 was recovered in the form of a matt dark-red powder.

The NMR and mass spectra were in accordance with compound 3.

Synthesis of Examples 1 to 4

The four Examples were synthesized according to the same procedure:

Compound 3 (2.61 mmol), the second dye (2.61 mmol), 1,3-dimethyl-3,4,5,6-tetrahydro-2(1H)-pyrimidinone (4 ml) and a catalytic amount (10%) of KI were placed in a round-bottomed flask at 95° C. for 14 hours. The products were then precipitated from ethyl acetate and then purified by chromatography.

Synthesis of Example 1 (Compound 5)

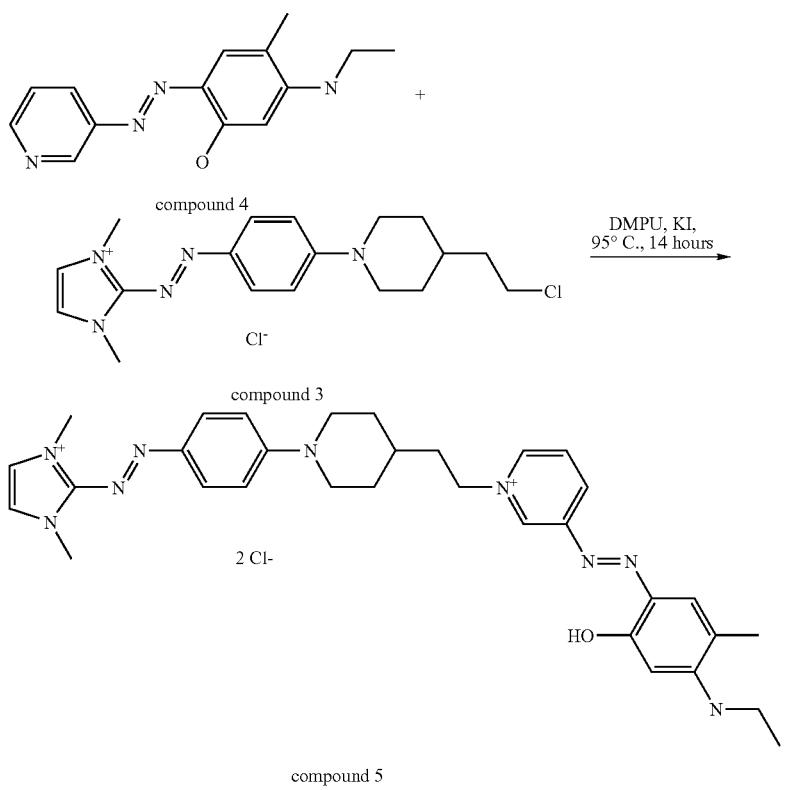

(Compound 4 was obtained by the coupling reaction of the diazonium salt of 3-aminopyridine with 3-(ethylamino)-4-methylphenol in acidic medium.)

Amounts Used:
Compound 4: 67 mg
Compound 3: 100 mg

The analyses performed were in accordance with the structure proposed for compound 5.

Dyeing Example 1

The composition below was prepared:

| Ingredients | Amount |
| --- | --- |
| (50/50 C8/C10) Alkyl polyglucoside (2) as a buffered 60% aqueous solution | 12 g |
| Pure absolute ethanol | 20 g |
| Pure benzyl alcohol | 4 g |
| Polyethylene glycol 400 (8 EO) | 6 g |
| Demineralized water | qs 100 g |

$5 \times 10^{-3}$ mol/l of compound 5 were dissolved in the composition described above.

The composition thus obtained was applied to locks of hair containing 90% white hairs.

An orange-red shade was obtained with compound 5.

Synthesis of Example 2 (Compound 7)

(Compound 6 was obtained according to the procedure described in the publication *Tetrahedron*, 1983, 39 (7), 1091-1101.)

Amounts Used:

Compound 6: 55.8 mg

Compound 3: 100 mg

The analyses performed were in accordance with the structure proposed for compound 7.

Dyeing Example 2

The process was performed as in Dyeing Example 1 above.

An orange-red shade was obtained with compound 7.

Synthesis of Example 3 (Compound 9)

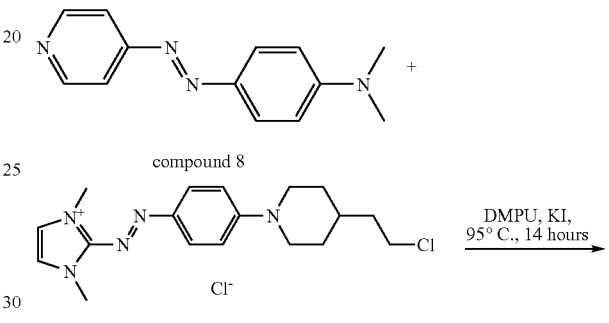

compound 8 compound 3

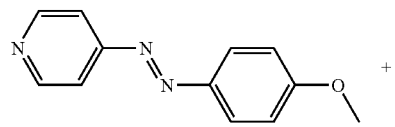

compound 6

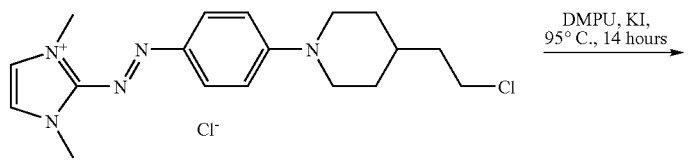

compound 3

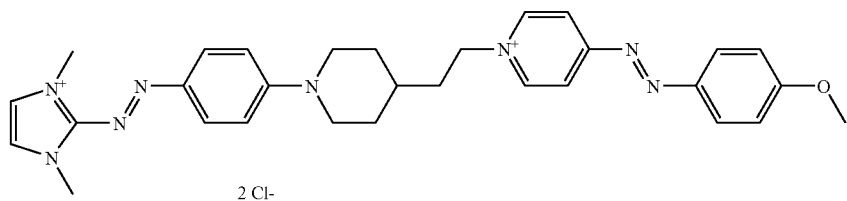

compound 7

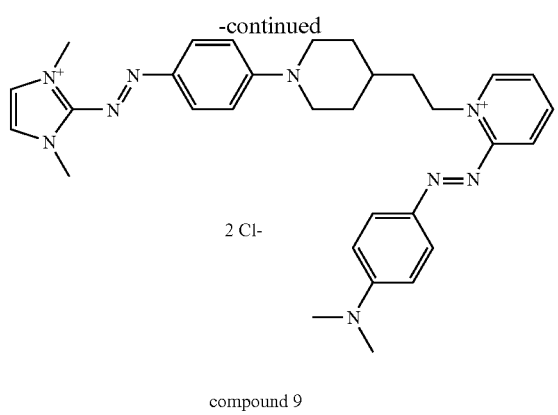

compound 9

(Compound 8 was a commercially available product.)
Amounts Used:
Compound 8: 59.2 mg
Compound 3: 100 mg
The analyses performed were in accordance with the structure proposed for compound 9.

Dyeing Example 3

The process was performed as in Dyeing Example 1 above.
A fast violet shade was obtained with compound 9.

Synthesis of Example 4 (Compound 11)

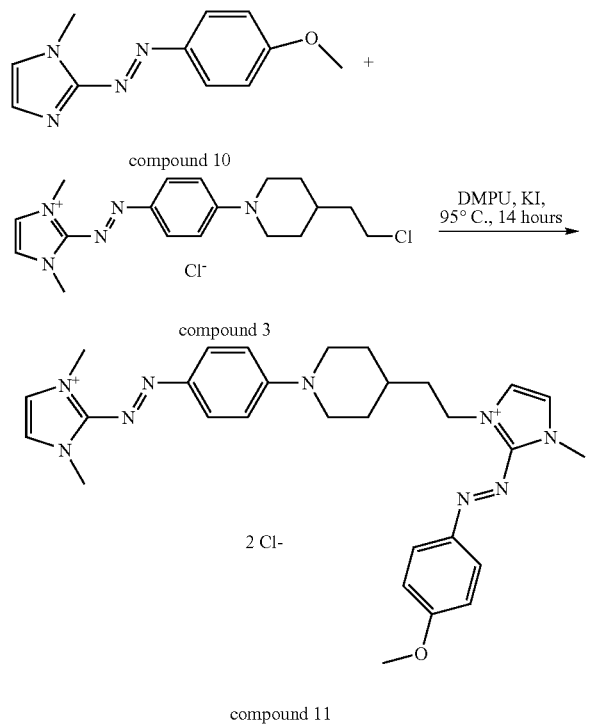

(Compound 10 was obtained in 3 steps:
coupling reaction of the diazonium salt of p-aminophenol with the imidazole.

O-alkylation reaction in acidic medium at reflux in methanol.
N-alkylation reaction in the presence of refluxing dimethyl carbonate and $K_2CO_3$.)
Amounts Used:
Compound 10: 56.6 mg
Compound 3: 100 mg
The analyses performed were in accordance with the structure proposed for compound 11.

Dyeing Example 4

The process was performed as in Dyeing Example 1 above.
A fuchsia-red shade was obtained with compound 11.

Example 5

Synthesis of Dye Example 5 (Compound 15)

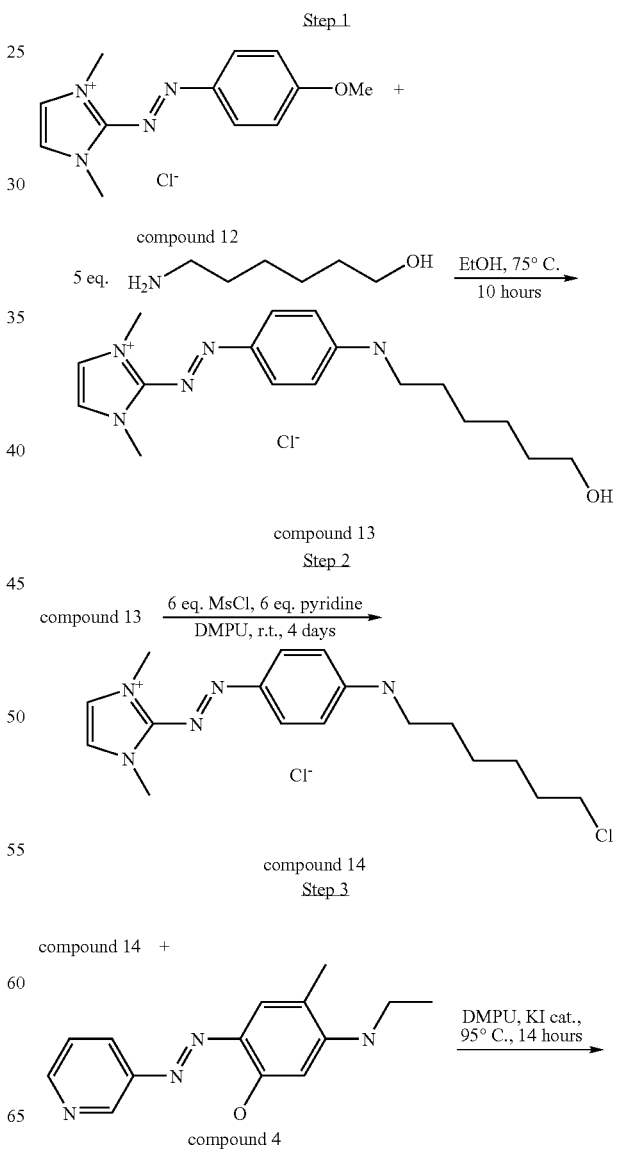

-continued

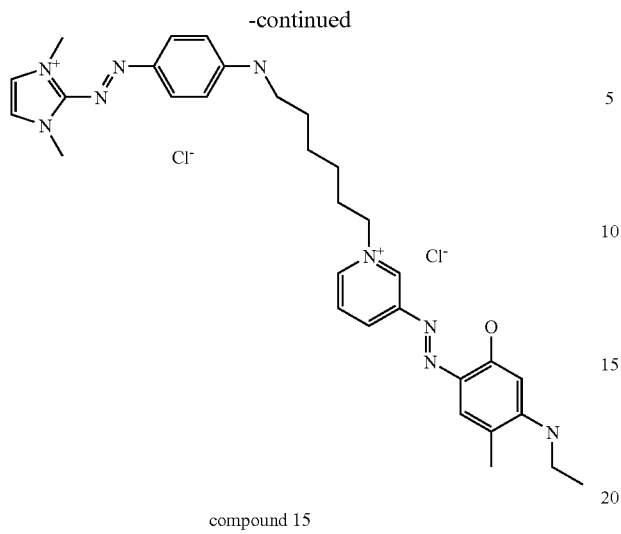

compound 15

Procedure

Step 1

Compound 12 (20 g) and ethanol (200 ml) were placed in a three-necked flask and 6-aminohexanol (43.9 g, 5 eq.) was added.

The mixture was heated to 70° C. (external temperature) with stirring.

After 10 hours, the heating was stopped and the mixture was allowed to cool to room temperature.

After evaporating off the solvent, compound 13 was recovered.

A red solid was obtained. The NMR and mass spectra were in accordance with compound 13.

Compound 13 (3 g), 1,3-dimethyl-3,4,5,6-tetrahydro-2 (1H)-pyrimidinone (80 ml), methanesulfonyl chloride (4 ml, 6 eq.) and pyridine (4.12 ml, 6 eq.) were placed in a three-necked flask.

The mixture was stirred at room temperature for 4 days.

The product was precipitated from ethyl acetate and then filtered off. The precipitate was dissolved in water and then extracted with dichloromethane. The organic phase was dried over sodium sulfate, filtered and then concentrated.

Compound 14 was recovered in the form of a matt red powder.

The NMR and mass spectra are in accordance with compound 14.

Step 3

Compounds 14 (100 mg) and 4 (69 mg), 1,3-dimethyl-3,4,5,6-tetrahydro-2(1H)-pyrimidinone (4 ml) and a catalytic amount of KI were placed in a three-necked flask.

The mixture was stirred at 95° C. for 14 hours.

The product was precipitated from ethyl acetate and then filtered off. The precipitate was purified by chromatography.

The analyses performed were in accordance with the structure proposed for compound 15.

Dyeing Example 5

The process was performed as in Dyeing Example 1 above.

An orange-red shade was obtained with compound 15.

What is claimed is:

1. A cationic compound chosen from those of formula (I) and the acid addition salts thereof:

$$Dye1\text{-}LK\text{-}Dye2 \quad (I)$$

wherein Dye1 and Dye2 are chosen from:

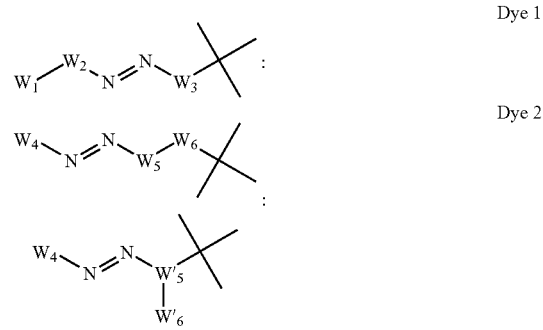

wherein:

W1 and W'$_6$, which may be identical or different, are chosen from —NR$_1$R$_2$ and —OR$_3$ groups, wherein R$_1$, R$_2$ and R$_3$, which may be identical or different, are chosen from hydrogen atoms and saturated and unsaturated, aromatic and non-aromatic, optionally substituted C$_1$-C$_{20}$ hydrocarbon-based chains, which can form at least one optionally substituted 3- to 7-membered carbon-based ring, optionally interrupted with at least one hetero atom or with at least one group bearing at least one hetero atom; R$_1$ and R$_2$ possibly forming, with the nitrogen atom to which they are attached, an optionally substituted 5- or 7-membered heterocycle optionally comprising another nitrogen or non-nitrogen hetero atom;

W$_6$ is chosen from —NR'$_1$— groups and —O— atoms, wherein R'$_1$, is chosen from a hydrogen atom and from saturated and unsaturated, aromatic and non-aromatic, optionally substituted C$_1$-C$_{20}$ hydrocarbon-based chains, which can form at least one optionally substituted 3- to 7-membered carbon-based ring, optionally interrupted with at least one hetero atom or with at least one group bearing at least one hetero atom;

the radicals R$_1$, R$_2$ and R$_3$ from W'$_6$, independently of each other, may optionally form with part of the group LK and with the nitrogen or oxygen atom to which each is attached a saturated or unsaturated, aromatic or non-aromatic, optionally substituted 5- to 7-membered heterocycle;

the radical R'$_1$ from W$_6$ may optionally form, with the nitrogen atom to which it is attached and a part of the group LK, a saturated or unsaturated, aromatic or non-aromatic, optionally substituted 5- to 7-membered heterocycle optionally comprising another hetero atom chosen from nitrogen and oxygen;

W$_2$, W$_5$ and W'$_5$, which may be identical or different, are chosen from the groups of formulae (a), (b), and (c):

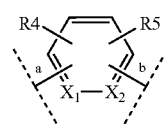

(a)

-continued (b)

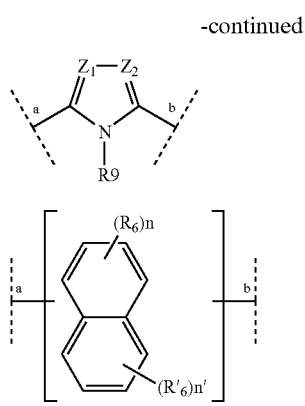

(c)

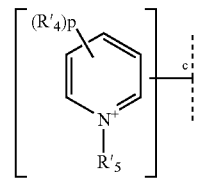

wherein:
X$_1$ is chosen from a nitrogen atom and CR$_7$ groups;
X$_2$ is chosen from a nitrogen atom and CR$_8$ groups;
Z$_1$ is chosen from a nitrogen atom and CR$_{10}$ groups;
Z$_2$ is chosen from a nitrogen atom and CR$_{11}$ groups;
R$_4$, R$_5$, R$_6$, R'$_6$, R$_7$, R$_8$, R$_{10}$ and R$_{11}$, which may be identical or different, are chosen from:
linear and branched, saturated and unsaturated, aromatic and non-aromatic, optionally substituted C$_1$-C$_{16}$ hydrocarbon-based chains, which can form at least one optionally substituted 3- to 6-membered carbon-based ring, optionally interrupted with at least one hetero atom or with at least one group bearing at least one hetero atom;
hydroxyl groups,
C$_1$-C$_4$ alkoxy groups,
C$_2$-C$_4$ (poly)hydroxyalkoxy groups;
alkoxycarbonyl groups (RO—CO—) in which R is chosen from C$_1$-C$_4$ alkyl radicals,
alkylcarbonyloxy radicals (RCO—O—) wherein R is chosen from C$_1$-C$_4$ alkyl radicals;
amino groups,
amino groups substituted with at least one C$_1$-C$_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
alkylcarbonylamino groups (RCO—NR—) in which the radicals R, which may be identical or different, are chosen from C$_1$-C$_4$ alkyl radicals;
carbamoyl groups ((R)$_2$N—CO) in which the radicals R, which may be identical or different, are chosen from hydrogen atoms and C$_1$-C$_4$ alkyl radicals;
ureido groups (N(R)$_2$—CO—NR'—) in which the radicals R and R', which may be identical or different, are chosen from hydrogen atoms and C$_1$-C$_4$ alkyl radicals;
sulfonamide groups ((R)$_2$N—SO$_2$—) in which the radicals R, which may be identical or different, are chosen from hydrogen atoms and C$_1$-C$_4$ alkyl radicals;
alkylsulfonylamino groups (RSO$_2$—NR'—) in which the radicals R and R', which may be identical or different, are chosen from hydrogen atoms and C$_1$-C$_4$ alkyl radicals;

guanidinium groups ((R')$_2$N—C(=NH$_2^+$)—NR—) in which the radicals R and R', which may be identical or different, are chosen from hydrogen atoms and C$_1$-C$_4$ alkyl radicals;
nitro groups;
cyano groups; and
halogen atoms;
wherein R$_4$, R$_5$, R$_7$, R$_8$, R$_{10}$ and R$_{11}$ may be a hydrogen atom; and
wherein R$_4$, R$_5$, R$_6$, R'$_6$, R$_7$, R$_8$, R$_{10}$ and R$_{11}$, independently of each other, may optionally form, with all or some of the groups W$_1$ or W'$_6$, a saturated or unsaturated, optionally substituted 5- to 7-membered heterocycle;
a bond from W'5 to W'6 or to the group LK;
a is the bond from W$_2$, W$_5$ or W'$_5$ to the azo group —N=N—;
b is the bond from W$_2$ to W$_1$, from W$_5$ to W$_6$, or from W'$_5$ to W'$_6$;
R$_9$ is chosen from:
a hydrogen atom,
linear and branched, saturated and unsaturated, aromatic and non-aromatic, optionally substituted C$_1$-C$_{16}$ hydrocarbon-based chains, which can form at least one optionally substituted 3- to 7-membered carbon-based ring,
n and n' are integers and the sum of n and n' is less than or equal to 6;
wherein when the sum of n and n' is less than 6, each missing substituent is a hydrogen atom;
W$_3$ and W$_4$, which may be identical or different, are cationic heteroaromatic radicals chosen from those of formulae (1) to (11):

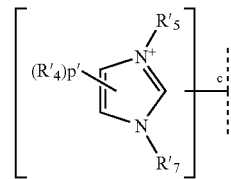 (1)

(2)

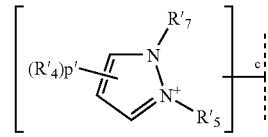 (3)

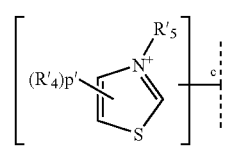 (4)

-continued

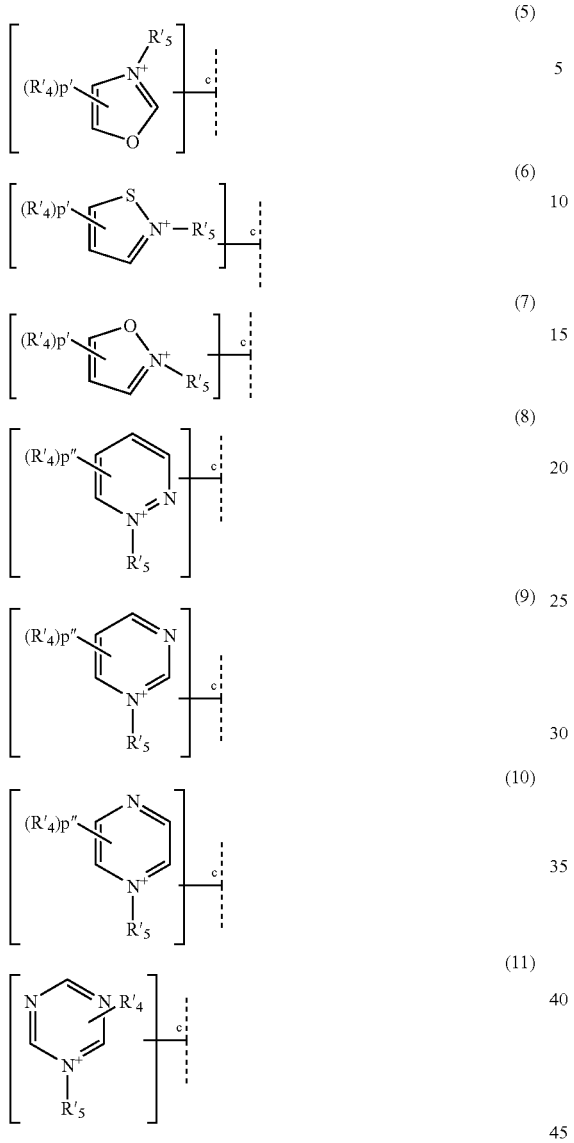

wherein:
R'₄, which may be identical or different, substituting the main ring, are chosen from:
- linear and branched, saturated and unsaturated, aromatic and non-aromatic, optionally substituted $C_1$-$C_{16}$ hydrocarbon-based chains, which can form at least one 3- to 6-membered carbon-based ring, optionally interrupted with at least one hetero atom or with at least one group bearing at least one hetero atom;
- hydroxyl groups,
- $C_1$-$C_4$ alkoxy groups,
- $C_2$-$C_4$ (poly)hydroxyalkoxy groups;
- alkoxycarbonyl groups (RO—CO—) in which R is chosen from $C_1$-$C_4$ alkyl radicals,
- alkylcarbonyloxy radicals (RCO—O—) in which R is chosen from $C_1$-$C_4$ alkyl radicals;
- amino groups,
- amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
- alkylcarbonylamino groups (RCO—NR'—) in which the radical R is chosen from $C_1$-$C_4$ alkyl radicals and the radical R' is chosen from a hydrogen atom and $C_1$-$C_4$ alkyl radicals;
- carbamoyl groups ($(R)_2$N—CO—) in which the radicals R, which may be identical or different, are chosen from hydrogen atoms and $C_1$-$C_4$ alkyl radicals;
- ureido groups (N(R)₂—CO—NR'—) in which the radicals R and R', which may be identical or different, are chosen from hydrogen atoms and $C_1$-$C_4$ alkyl radicals;
- sulfonamide groups ($(R)_2$N—SO₂—) in which the radicals R, which may be identical or different, are chosen from hydrogen atoms and $C_1$-$C_4$ alkyl radicals;
- alkylsulfonylamino groups (RSO₂—NR'—) in which the radicals R and R', which may be identical or different, are chosen from hydrogen atoms and $C_1$-$C_4$ alkyl radicals;
- guanidinium groups ($(R')_2$N—C(=NH₂⁺)—NR—) in which the radicals R and R', which may be identical or different, are chosen from hydrogen atoms and $C_1$-$C_4$ alkyl radicals;
- nitro groups; cyano groups; and halogen atoms;
- wherein two radicals R'₄ borne by two adjacent carbon atoms of the main ring may optionally form an aromatic or non-aromatic, 5- or 6-membered secondary ring, optionally substituted with at least one entity chosen from hydrogen atoms, hydroxyl groups, $C_1$-$C_4$ alkyl radicals, a $C_1$-$C_4$ alkoxy radicals, $C_2$-$C_4$(poly)hydroxyalkoxy radicals, amino radicals, and amino radicals substituted with at least one or more $C_1$-$C_4$ alkyl radical, which may be identical or different, optionally bearing at least one hydroxyl group;

R'₅, borne by the quaternized nitrogen atom, in the case of W₄, is chosen from linear and branched, saturated and unsaturated, aromatic and non-aromatic, optionally substituted $C_1$-$C_{16}$ hydrocarbon-based chains, which can form at least one optionally substituted 3- to 6-membered carbon-based ring, optionally interrupted with at least one hetero atom or with at least one group bearing at least one hetero atom; the radical R'₅ is such that the atom directly linked to the quaternized nitrogen atom is a carbon atom;

R'₅ borne by the quaternized nitrogen atom, in the case of W₃, is a bond to LK;

R'₇ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2 and p" is an integer ranging from 0 to 3; wherein when the main ring does not bear the maximum number of substituents, then the unsubstituted position bears a nitrogen atom;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom; with the proviso that the group LK does not comprise any peroxo, nitro or nitroso groups or bonds; if LK is linked to $W'_5$, LK may end with a hetero atom or group comprising at least one hetero atom; if LK is linked to $W_6$, LK may end with a group comprising at least one hetero atom chosen from —CO— and —SO$_2$— groups; if LK is linked to $W_3$, the bonding takes place via a carbon atom;

wherein LK does not bear any cationic charge; and wherein the electrical neutrality of the compounds is ensured by at least one cosmetically acceptable anion (An).

2. The compound according to claim 1, wherein $R_1$, $R_2$, $R_3$ and $R'_1$, which may be identical or different, are chosen from:

hydrogen atoms;

optionally substituted $C_1$-$C_6$ alkyl radicals; and aryl and arylalkyl radicals, the aryl part being optionally substituted;

wherein the radicals $R_1$, $R_2$, $R_3$ from $W'_6$, independently of each other, can optionally form, with part of the group LK and with the nitrogen or oxygen atom to which each is attached, a saturated or unsaturated, aromatic or non-aromatic, optionally substituted 5- to 7-membered heterocycle;

wherein the radical $R'_1$ from $W_6$ may optionally form, with the nitrogen atom to which it is attached and a part of the group LK, a saturated or unsaturated, aromatic or non-aromatic, optionally substituted 5-, 6- or 7-membered heterocycle optionally comprising another hetero atom chosen from nitrogen and oxygen.

3. The compound according to claim 1, wherein the radicals $R_1$, $R_2$, $R_3$ and $R'_1$, which may be identical or different, are chosen from:

hydrogen atoms;

optionally substituted $C_1$-$C_3$ alkyl radicals; and phenyl radicals, optionally substituted with at least one radical chosen from hydroxyl; $C_1$-$C_2$ alkoxy and amino radicals, and amino radicals substituted with at least one $C_1$-$C_4$ group optionally bearing at least one hydroxyl group;

wherein the radical $R'_1$ from $W_6$ can form, with the nitrogen atom to which it is attached and part of the group LK, a 5- or 6-membered heterocycle chosen from pyrrolidine, piperidine, piperazine and homopiperazine and optionally substituted with at least one radical chosen from methyl, hydroxyl, amino and (di)methylamino radicals.

4. The compound according to claim 1, wherein $R_1$, $R_2$, $R_3$ and $R'_1$, which may be identical or different, are chosen from:

hydrogen atoms;

methyl, ethyl, and 2-hydroxyethyl radicals; and phenyl radicals, optionally substituted with a hydroxyl, methoxy, amino, (di)methylamino or (di)(2-hydroxyethyl)amino radical;

wherein the radical $R'_1$ from $W_6$ can form, with the nitrogen atom to which it is attached and part of the group LK, a 5- to 7-membered heterocycle.

5. The compound according to claim 1, wherein the radicals $R_4$, $R_5$, $R_6$, $R'_6$, $R_7$, $R_8$, $R_9$, $R_{10}$ and $R_{11}$, which may be identical or different, are chosen from:

hydrogen atoms for $R_4$, $R_5$, $R_7$, $R_8$, $R_{10}$ and $R_{11}$;

optionally substituted $C_1$-$C_{16}$ alkyl radicals;

halogen atoms;

hydroxyl groups;

$C_1$-$C_2$ alkoxy radicals;

$C_2$-$C_4$ (poly)hydroxyalkoxy radicals;

amino radicals;

amino radicals substituted with one or two $C_1$-$C_4$ alkyl radicals, which may be identical or different, optionally bearing at least one hydroxyl or $C_1$-$C_4$ dialkylamino group;

alkylcarbonylamino radicals (RCO—NR'—) in which the radical R is chosen from $C_1$-$C_4$ alkyl radicals and the radical R' is chosen from a hydrogen and $C_1$-$C_4$ alkyl radicals;

carbamoyl radicals ((R)$_2$N—CO—) in which the radicals R, which may be identical or different, are chosen from hydrogen atoms and $C_1$-$C_4$ alkyl radicals optionally bearing at least one hydroxyl group;

alkylsulfonylamino radicals (R'SO$_2$—NR—) in which the radical R is chosen from hydrogen atoms and $C_1$-$C_4$ alkyl radicals optionally bearing at least one hydroxyl group, the radical R' is chosen from $C_1$-$C_4$ alkyl radicals;

aminosulfonyl radicals ((R)$_2$N—SO$_2$—) in which the radicals R, which may be identical or different, are chosen from hydrogen atoms and $C_1$-$C_4$ alkyl radicals optionally bearing at least one hydroxyl group; and a bond from $W'_5$ to $W'_6$.

6. The compound according to claim 1, wherein the radicals $R_4$, $R_5$, $R_6$, $R'_6$, $R_7$, $R_8$, $R_9$, $R_{10}$ and $R_{11}$, which may be identical or different, are chosen from:

hydrogen atoms for $R_4$, $R_5$, $R_7$, $R_8$, $R_{10}$ and $R_{11}$;

$C_1$-$C_4$ alkyl radicals optionally substituted with at least one radical chosen from hydroxyl and acylamino radicals, or amino radicals substituted with two identical or different $C_1$-$C_2$ alkyl radicals, optionally bearing at least one hydroxyl group, or a $C_1$-$C_2$ alkoxy radical;

amino radicals;

amino radicals substituted with one or two identical or different $C_1$-$C_2$ alkyl radicals, optionally bearing at least one hydroxyl group;

acylamino radicals;

carbamoyl radicals;

sulfonylamino radicals;

hydroxyl radicals;

$C_1$-$C_2$ alkoxy radicals; and a bond from $W'_5$ to $W'_6$.

7. The compound according to claim 1, wherein $W_2$, $W_5$ and $W'_5$, which may be identical or different, are chosen from the compounds of formula (a) and (c).

8. The compound according to claim 1, wherein $X_1$ is chosen from $CR_7$ radicals.

9. The compound according to claim 8, wherein $X_2$ is chosen from $CR_8$ groups.

10. The compound according to claim 1, wherein $W_3$ and $W_4$, which may be identical or different, are heterocycles chosen from those of formulae (1), (2), and (3):

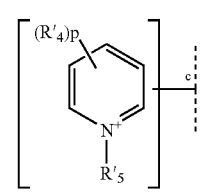

(1)

-continued

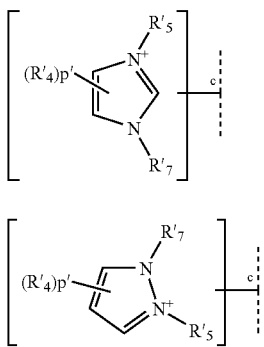

wherein R'$_4$, R'$_5$, R'$_7$, p, p' and a are as defined in claim 1.

11. The compound according to claim 10, wherein the heterocycles are chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium;

wherein at least one of the two groups W$_3$ or W$_4$ is not an unsubstituted imidazolium group.

12. The compound according to claim 1, wherein LK is chosen from linear, branched and cyclic, and aromatic and non-aromatic C$_1$-C$_{20}$ alkyl chains:

optionally interrupted with at least one hetero atom and/or group comprising at least one hetero atom, on condition that there are no nitro, nitroso or peroxo groups or bonds in the group LK;

optionally ending with a hetero atom or group bearing at least one hetero atom, if LK is linked to W'$_5$;

optionally ending with a group bearing at least one hetero atom chosen from —CO— and —SO$_2$— if LK is linked to W$_6$;

if LK is linked to W$_3$ via a quaternized nitrogen atom, LK is directly linked to W$_3$ via a carbon atom;

optionally substituted with at least one radical chosen from hydroxyl, C$_1$-C$_2$ alkoxy, and C$_2$-C$_4$ (poly)hydroxyalkoxy radicals, and amino radicals substituted with at least one linear or branched C$_1$-C$_2$ alkyl group optionally bearing at least one hydroxyl group.

13. The compound according to claim 1, chosen from those of the formulae:

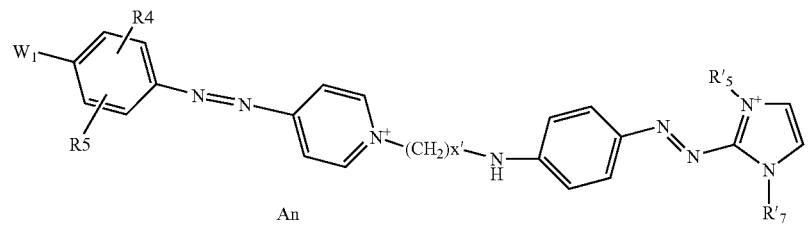

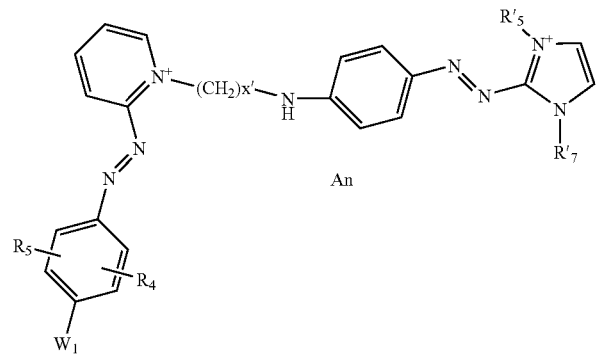

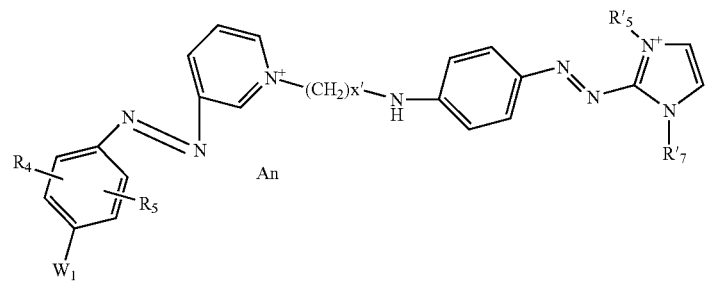

-continued

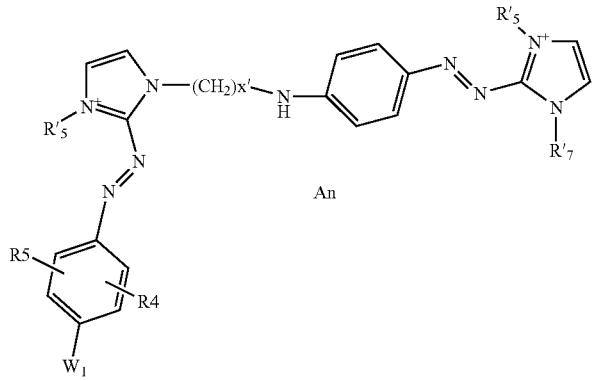

wherein $W_1$, $R_4$, $R_5$, $R'_5$ and $R'_7$ are as defined in claim 1; and x and x', which may be identical or different, are integers ranging from 1 to 10;

the electrical neutrality of the molecule being respected by the presence of the at least one cosmetically acceptable anions An as defined above.

14. The cationic dye compound according to claim 1, wherein the at least one cosmetically acceptable anion is chosen from halides; hydroxides; sulfates; hydrogen sulfates; ($C_1$-$C_6$)alkyl sulfates; carbonates; hydrogen carbonates; perchlorates; acetates; tartrates; citrates; oxalates; ($C_1$-$C_6$)alkylsulfonates; arylsulfonates, which are unsubstituted or substituted with a $C_1$-$C_4$ alkyl radical.

15. A dye composition comprising, in a medium that is suitable for dyeing keratin fibers, as direct dye, at least one compound chosen from those of formula (I) and the acid addition salts thereof:

Dye1-LK-Dye2 (I)

wherein Dye1 and Dye2 are chosen from:

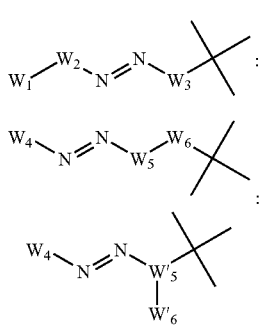

Dye 1

Dye 2 wherein:

W1 and $W'_6$, which may be identical or different, are chosen from —$NR_1R_2$ and —$OR_3$ groups, wherein $R_1$, $R_2$ and $R_3$, which may be identical or different, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one groups bearing at least one hetero atom; $R_1$ and $R_2$ possibly forming, with the nitrogen atom to which they are attached, an optionally substituted 5- or 7-membered heterocycle optionally comprising another nitrogen or non-nitrogen hetero atom;

$W_6$ is chosen from —$NR'_1$— groups and —O— atoms, wherein $R'_1$ is chosen from a hydrogen atom and from saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom;

the radicals $R_1$, $R_2$ and $R_3$ from $W'_6$, independently of each other, may optionally form with part of the group LK and with the nitrogen or oxygen atom to which each is attached a saturated or unsaturated, aromatic or non-aromatic, optionally substituted 5- to 7-membered heterocycle;

the radical $R'_1$ from $W_6$ may optionally form, with the nitrogen atom to which it is attached and a part of the group LK, a saturated or unsaturated, aromatic or non-aromatic, optionally substituted 5- to 7-membered heterocycle optionally comprising another hetero atom chosen from nitrogen and oxygen;

$W_2$, $W_5$ and $W'_5$, which may be identical or different, are chosen from the groups of formulae (a), (b), and (c):

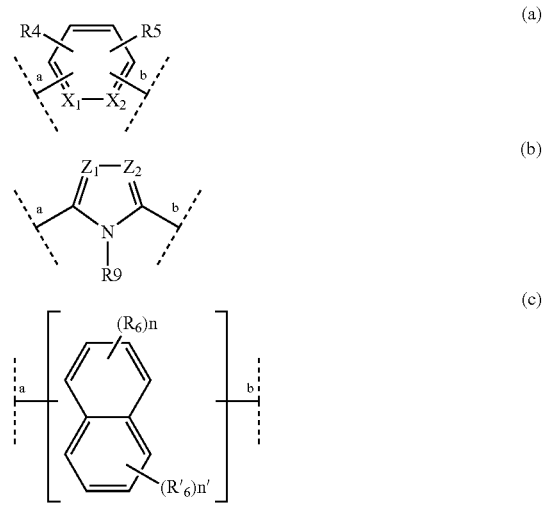

wherein:

$X_1$ is chosen from a nitrogen atom and $CR_7$ groups;

$X_2$ is chosen from a nitrogen atom and $CR_8$ groups;

$Z_1$ is chosen from a nitrogen atom and $CR_{10}$ groups;

$Z_2$ is chosen from a nitrogen atom and $CR_{11}$ groups;

$R_4$, $R_5$, $R_6$, $R'_6$, $R_7$, $R_8$, $R_{10}$ and $R_{11}$, which may be identical or different, are chosen from:

linear and branched, saturated and unsaturated, aromatic and non-aromatic, optionally substituted $C_1$-$C_{16}$ hydrocarbon-based chains, which can form at least one optionally substituted 3- to 6-membered carbon-based ring, optionally interrupted with at least one hetero atom or with at least one group bearing at least one hetero atom;

hydroxyl groups, $C_1$-$C_4$ alkoxy groups, $C_2$-$C_4$ (poly)hydroxyalkoxy groups;

alkoxycarbonyl groups (RO—CO—) in which R is chosen from $C_1$-$C_4$ alkyl radicals, alkylcarbonyloxy radicals (RCO—O—) wherein R is chosen from $C_1$-$C_4$ alkyl radicals;

amino groups, amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR—) in which the radicals R, which may be identical or different, are chosen from $C_1$-$C_4$ alkyl radicals;

carbamoyl groups ((R)$_2$N—CO) in which the radicals R, which may be identical or different, are chosen from hydrogen atoms and $C_1$-$C_4$ alkyl radicals;

ureido groups (N(R)$_2$—CO—NR'—) in which the radicals R and R', which may be identical or different, are chosen from hydrogen atoms and $C_1$-$C_4$ alkyl radicals;

sulfonamide groups ((R)$_2$N—SO$_2$—) in which the radicals R, which may be identical or different, are chosen from hydrogen atoms and $C_1$-$C_4$ alkyl radicals;

alkylsulfonylamino groups (RSO$_2$—NR'—) in which the radicals R and R', which may be identical or different, are chosen from hydrogen atoms and $C_1$-$C_4$ alkyl radicals;

guanidinium groups ((R')$_2$N—C(=NH$_2^+$)—NR—) in which the radicals R and R', which may be identical or different, are chosen from hydrogen atoms and $C_1$-$C_4$ alkyl radicals;

nitro groups; cyano groups; and halogen atoms;

wherein $R_4$, $R_5$, $R_7$, $R_8$, $R_{10}$ and $R_{11}$, may be a hydrogen atom; and wherein $R_4$, —$R_5$, $R_6$, $R'_6$, $R_7$, $R_8$, $R_{10}$ and $R_{11}$, independently of each other, may optionally form, with all or some of the groups $W_1$ or $W'_6$, a saturated or unsaturated, optionally substituted 5- to 7-membered heterocycle;

a bond from W'5 to W'6 or to the group LK;

a is the bond from $W_2$, $W_5$ or $W'_5$ to the azo group —N=N—;

b is the bond from $W_2$ to $W_1$, from $W_5$ to $W_6$, or from $W'_5$ to $W'_6$;

$R_9$ is chosen from:

a hydrogen atom, linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

wherein when the sum of n and n' is less than 6, each missing substituent is a hydrogen atom;

$W_3$ and $W_4$, which may be identical or different, are cationic heteroaromatic radicals chosen from those of formulae (1) to (11):

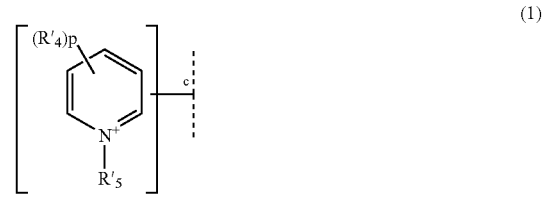

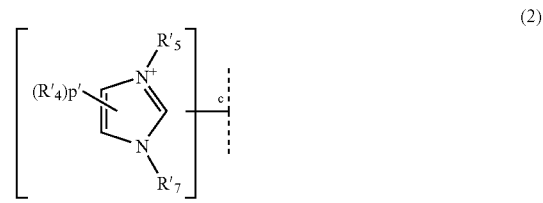

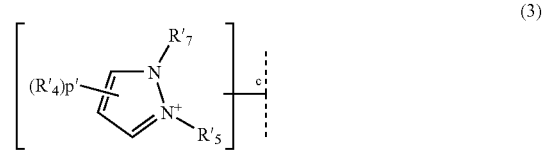

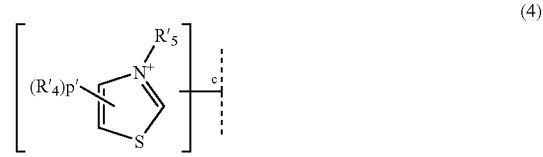

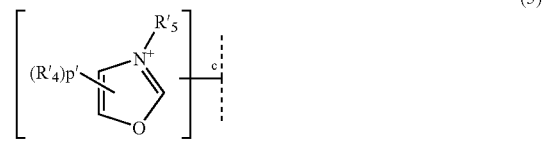

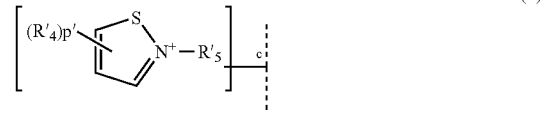

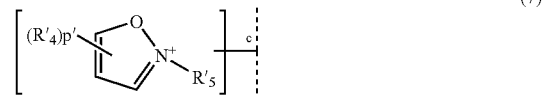

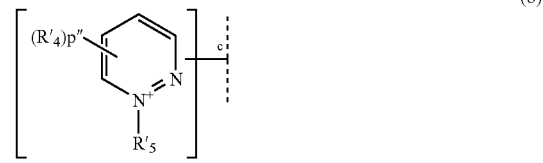

-continued

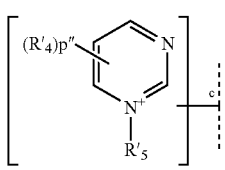
(9)

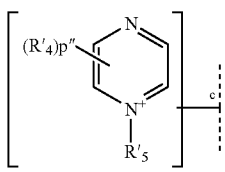
(10)

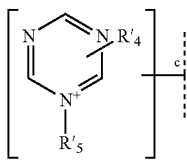
(11)

wherein:
R'$_4$, which may be identical or different, substituting the main ring, are chosen from:
  linear and branched, saturated and unsaturated, aromatic and non-aromatic, optionally substituted C$_1$-C$_{16}$ hydrocarbon-based chains, which can form at least one 3- to 6-membered carbon-based ring, optionally interrupted with at least one hetero atom or with at least one group bearing at least one hetero atom;
  hydroxyl groups,
  C$_1$-C$_4$ alkoxy groups,
  C$_2$-C$_4$ (poly)hydroxyalkoxy groups;
  alkoxycarbonyl groups (RO—CO—) in which R is chosen from C$_1$-C$_4$ alkyl radicals,
  alkylcarbonyloxy radicals (RCO—O—) in which R is chosen from C$_1$-C$_4$ alkyl radicals;
  amino groups,
  amino groups substituted with at least one C$_1$-C$_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR'—) in which the radical R is chosen from C$_1$-C$_4$ alkyl radicals and the radical R' is chosen from a hydrogen atom and C$_1$-C$_4$ alkyl radicals;
  carbamoyl groups ((R)$_2$N—CO—) in which the radicals R, which may be identical or different, are chosen from hydrogen atoms and C$_1$-C$_4$ alkyl radicals;
  ureido groups (N(R)$_2$—CO—NR'—) in which the radicals R and R', which may be identical or different, are chosen from hydrogen atoms and C$_1$-C$_4$ alkyl radicals;
  sulfonamide groups (R)$_2$N—SO$_2$—) in which the radicals R, which may be identical or different, are chosen from hydrogen atoms and C$_1$-C$_4$ alkyl radicals;
  alkylsulfonylamino groups (RSO$_2$—NR'—) in which the radicals R and R', which may be identical or different, are chosen from hydrogen atoms and C$_1$-C$_4$ alkyl radicals;
  guanidinium groups ((R')$_2$N—C(=NH$_2$$^+$)—NR—) in which the radicals R and R', which may be identical or different, are chosen from hydrogen atoms and C$_1$-C$_4$ alkyl radicals;
  nitro groups; cyano groups; and halogen atoms;
  wherein two radicals R'$_4$ borne by two adjacent carbon atoms of the main ring may optionally form an aromatic or non-aromatic, 5- or 6-membered secondary ring, optionally substituted with at least one entity chosen from hydrogen atoms, hydroxyl groups, C$_1$-C$_4$ alkyl radicals, C$_1$-C$_4$ alkoxy radicals, C$_2$-C$_4$(poly)hydroxyalkoxy radicals, amino radicals, and amino radicals substituted with at least one C$_1$-C$_4$ alkyl radical, which may be identical or different, optionally bearing at least one hydroxyl group;
R'$_5$, borne by the quaternized nitrogen atom, in the case of W$_4$, is chosen from linear and branched, saturated and unsaturated, aromatic and non-aromatic, optionally substituted C$_1$-C$_{16}$ hydrocarbon-based chains, which can form at least one optionally substituted 3- to 6-membered carbon-based ring, optionally interrupted with at least one hetero atom or with at least one group bearing at least one hetero atom; the radical R'$_5$ is such that the atom directly linked to the quaternized nitrogen atom is a carbon atom;
R'$_5$ borne by the quaternized nitrogen atom, in the case of W$_3$, is a bond to LK;
R'$_7$ is chosen from optionally substituted C$_1$-C$_4$ alkyl radicals; optionally substituted phenyl radicals; and optionally substituted benzyl radicals;
the bond c links the cationic radical defined by formulae (1) to (11) to the azo group; the bond may be on the main or secondary ring;
p is an integer ranging from 0 to 4, p' is an integer ranging from 0 to 2 and p" is an integer ranging from 0 to 3; wherein when the main ring does not bear the maximum number of substituents, then the unsubstituted position bears a nitrogen atom;
LK is chosen from saturated and unsaturated, linear and branched, cyclic and non-cyclic, aromatic and non-aromatic, optionally substituted C$_2$-C$_{40}$ hydrocarbon-based chains, optionally interrupted with at least one hetero atom or group comprising at least one hetero atom; with the proviso that the group LK does not comprise any peroxo, nitro or nitroso groups or bonds; if LK is linked to W'$_5$, LK may end with a hetero atom or group comprising at least one hetero atom; if LK is linked to W$_6$, LK may end with a group comprising at least one hetero atom chosen from —CO— and —SO$_2$— groups; if LK is linked to W$_3$, the bonding takes place via a carbon atom;
wherein LK does not bear any cationic charge; and
wherein the electrical neutrality of the compounds is ensured by at least one cosmetically acceptable anions (An).

16. The dye composition according to claim 15, wherein the at least one compound chosen from those of formula (I) and the acid addition salts thereof is present in an amount ranging from 0.001% to 20% by weight, relative to the total weight of the dye composition.

17. The dye composition according to claim 16, wherein the at least one compound chosen from those of formula (I) and the acid addition salts thereof is present in an amount ranging from 0.01% and 10% by weight, relative to the total weight of the dye composition.

18. The dye composition according to claim 15, further comprising at least one at least one color modifier chosen from additional direct dyes different from the first direct dye, and oxidation bases optionally combined with at least one coupler.

19. The dye composition according to claim 18, wherein the at least one additional direct dye different from the first dye is a cationic or nonionic dye chosen from nitrobenzene dyes, azo, azomethine, methine, tetraazapentamethine, anthraquinone, naphthoquinone, berizoquinone, phenothiazine, indigoid, xanthene, phenanthridine, phthalocyanin and triarylmethane-based dyes, and natural dyes.

20. The dye composition according to claim 18, wherein the at least one oxidation base is chosen from o-phenylenediamines, p-phenylenediamines, double bases, o-aminophenols, p-aminophenols, heterocyclic bases, and the acid addition salts thereof.

21. The dye composition according to claim 18, wherein the at least one coupler is chosen from m-aminophenols, m-phenylenediamines, m-diphenols, naphthols, heterocyclic couplers, and the acid addition salts thereof.

22. The dye composition according to claim 15, further comprising at least one oxidizing agent.

23. A process for dyeing keratin fibers, comprising
    applying to wet or dry keratin fibers, a composition comprising, in a medium that is suitable for dyeing keratin fibers, as a direct dye, at least one compound chosen from those of formula (I) and the acid addition salts thereof, and
    leaving the composition on the keratin fibers for a period of time that is sufficient to obtain the desired effect:

Dye1-LK-Dye2  (I)

wherein Dye1 and Dye2 are chosen from:

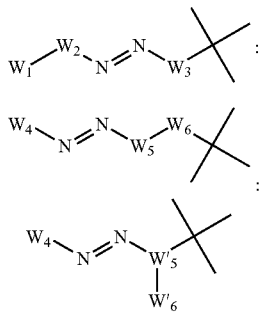

Dye 1

Dye 2 wherein:
W$_1$ and W'$_6$, which may be identical or different, are chosen from —NR$_1$R$_2$ and —OR$_3$ groups, wherein R$_1$, R$_2$ and R$_3$, which may be identical or different, are chosen from hydrogen atoms and saturated and unsaturated, aromatic and non-aromatic, optionally substituted C$_1$-C$_{20}$ hydrocarbon-based chains, which can form at least one optionally substituted 3- to 7-membered carbon-based ring, optionally interrupted with at least one hetero atom or with at least one group bearing at least one hetero atom; R$_1$ and R$_2$ possibly forming, with the nitrogen atom to which they are attached, an optionally substituted 5- or 7-membered heterocycle optionally comprising another nitrogen or non-nitrogen hetero atom;

W$_6$ is chosen from —NR'$_1$— groups and —O— atoms, wherein R'$_1$ is chosen from a hydrogen atom and saturated and unsaturated, aromatic and non-aromatic, optionally substituted C$_1$-C$_{20}$ hydrocarbon-based chains, which can form at least one optionally substituted 3- to 7-membered carbon-based ring, optionally interrupted with at least one hetero atom or with at least one group bearing at least one hetero atom;

the radicals R$_1$, R$_2$ and R$_3$ from W'$_6$, independently of each other, may optionally form with part of the group LK and with the nitrogen or oxygen atom to which each is attached a saturated or unsaturated, aromatic or non-aromatic, optionally substituted 5- to 7-membered heterocycle;

the radical R'$_1$ from W$_6$ may optionally form, with the nitrogen atom to which it is attached and a part of the group LK, a saturated or unsaturated, aromatic or non-aromatic, optionally substituted 5- to 7-membered heterocycle optionally comprising another hetero atom chosen from nitrogen and oxygen;

W$_2$, W$_5$ and W'$_5$, which may be identical or different, are chosen from the groups of formulae (a), (b), and (c):

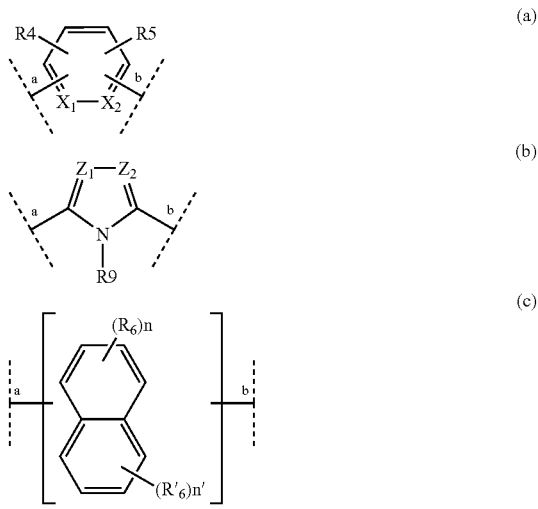

wherein:
X$_1$ is chosen from a nitrogen atom and CR$_7$ groups;
X$_2$ is chosen from a nitrogen atom and CR$_8$ groups;
Z$_1$ is chosen from a nitrogen atom and CR$_{10}$ groups;
Z$_2$ is chosen from a nitrogen atom and CR$_{11}$ groups;
R$_4$, R$_5$, R$_6$, R'$_6$, R$_7$, R$_8$, R$_{10}$ and R$_{11}$ which may be identical or different, are chosen from:
    linear and branched, saturated and unsaturated, aromatic and non-aromatic, optionally substituted C$_1$-C$_{15}$ hydrocarbon-based chains, which can form at least one optionally substituted 3- to 6-membered carbon-based ring, optionally interrupted with at least one hetero atom or with at least one group bearing at least one hetero atom;
    hydroxyl groups,
    C$_1$-C$_4$ alkoxy groups,
    C$_2$-C$_4$ (poly)hydroxyalkoxy groups;
    alkoxycarbonyl groups (RO—CO—) in which R is chosen from C$_1$-C$_4$ alkyl radicals,
    alkylcarbonyloxy radicals (RCO—O—) wherein R is chosen from C$_1$-C$_4$ alkyl radicals;
    amino groups, amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR—) in which the radicals R, which may be identical or different, are chosen from $C_1$-$C_4$ alkyl radicals;

carbamoyl groups (($R)_2$N—CO) in which the radicals R, which may be identical or different, are chosen from hydrogen atoms and $C_1$-$C_4$ alkyl radicals;

ureido groups (N(R)$_2$—CO—NR'—) in which the radicals R and R', which may be identical or different, are chosen from hydrogen atoms and $C_1$-$C_4$ alkyl radicals;

sulfonamide groups (($R)_2$N—$SO_2$—) in which the radicals R, which may be identical or different, are chosen from hydrogen atoms and $C_1$-$C_4$ alkyl radicals;

alkylsulfonylamino groups ($RSO_2$—NR'—) in which the radicals R and R', which may be identical or different, are chosen from hydrogen atoms and $C_1$-$C_4$ alkyl radicals;

guanidinium groups ((R')$_2$N—C(=$NH_2^+$)—NR—) in which the radicals R and R', which may be identical or different, are chosen from hydrogen atoms and $C_1$-$C_4$ alkyl radicals;

nitro groups; cyano groups; and halogen atoms;

wherein $R_4$, $R_5$, $R_7$, $R_8$, $R_{10}$ and $R_{11}$ may be a hydrogen atom; and wherein $R_4$, $R_5$, $R_6$, $R'_6$, $R_7$, $R_8$, $R_{10}$ and $R_{11}$, independently of each other, may optionally form, with all or some of the groups $W_1$ or $W'_6$, a saturated or unsaturated, optionally substituted 5- to 7-membered heterocycle;

a bond from W'5 to W'6 or to the group LK;

a is the bond from $W_2$, $W_5$ or $W'_5$ to the azo group —N=N—;

b is the bond from $W_2$ to $W_1$, from $W_5$ to $W_6$, or from $W'_5$ to $W'_6$;

$R_9$ is chosen from:
 a hydrogen atom,
 linear and branched, saturated and unsaturated, aromatic and non-aromatic, optionally substituted $C_1$-$C_{15}$ hydrocarbon-based chains, which can form at least one optionally substituted 3- to 7-membered carbon-based ring, n and n' are integers and the sum of n and n' is less than or equal to 6;

wherein when the sum of n and n' is less than 6, each missing substituent is a hydrogen atom;

$W_3$ and $W_4$, which may be identical or different, are cationic heteroaromatic radicals chosen from those of formulae (1) to (11):

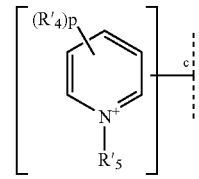
(1)

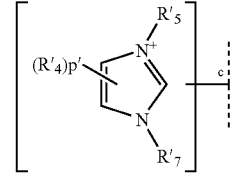
(2)

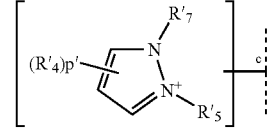
(3)

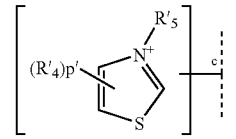
(4)

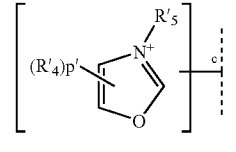
(5)

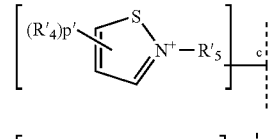
(6)

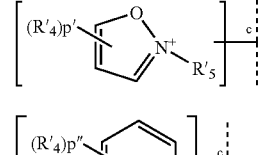
(7)

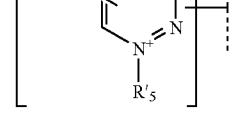
(8)

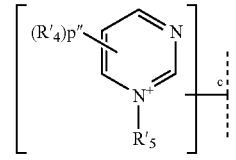
(9)

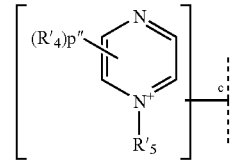
(10)

-continued

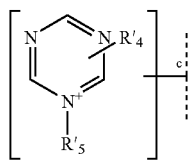

(11)

wherein:
R'₄, which may be identical or different, substituting the main ring, are chosen from:
linear and branched, saturated and unsaturated, aromatic and non-aromatic, optionally substituted $C_1$-$C_{15}$ hydrocarbon-based chains, which can form at least one 3- to 6-membered carbon-based ring, optionally interrupted with at least one hetero atom or with at least one group bearing at least one hetero atom;
hydroxyl groups,
$C_1$-$C_4$ alkoxy groups,
$C_2$-$C_4$ (poly)hydroxyalkoxy groups;
alkoxycarbonyl groups (RO—CO—) in which R is chosen from $C_1$-$C_4$ alkyl radicals,
alkylcarbonyloxy radicals (RCO—O—) in which R is chosen from $C_1$-$C_4$ alkyl radicals;
amino groups,
amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
alkylcarbonylamino groups (RCO—NR'—) in which the radical R is chosen from $C_1$-$C_4$ alkyl radicals and the radical R' is chosen from a hydrogen atom and $C_1$-$C_4$ alkyl radicals;
carbamoyl groups ((R)₂N—CO—) in which the radicals R, which may be identical or different, are chosen from hydrogen atoms and $C_1$-$C_4$ alkyl radicals;
ureido groups (N(R)₂—CO—NR'—) in which the radicals R and R', which may be identical or different, are chosen from hydrogen atoms and $C_1$-$C_4$ alkyl radicals;
sulfonamide groups ((R)₂N—SO₂—) in which the radicals R, which may be identical or different, are chosen from hydrogen atoms and $C_1$-$C_4$ alkyl radicals;
alkylsulfonylamino groups (RSO₂—NR'—) in which the radicals R and R', which may be identical or different, are chosen from hydrogen atoms and $C_1$-$C_4$ alkyl radicals;
guanidinium groups ((R')₂N—C(=NH₂⁺)—NR—) in which the radicals R and R', which may be identical or different, are chosen from hydrogen atoms and $C_1$-$C_4$ alkyl radicals;
nitro groups; cyano groups; and halogen atoms;
wherein two radicals R'₄ borne by two adjacent carbon atoms of the main ring may optionally form an aromatic or non-aromatic, 5- or 6-membered secondary ring, optionally substituted with at least one entity chosen from hydrogen atoms, hydroxyl groups, $C_1$-$C_4$ alkyl radicals, $C_1$-$C_4$ alkoxy radicals, $C_2$-$C_4$(poly)hydroxyalkoxy radicals, amino radicals, and amino radicals substituted with at least one $C_1$-$C_4$ alkyl radical, which may be identical or different, optionally bearing at least one hydroxyl group;

R'₅, borne by the quaternized nitrogen atom, in the case of W₄, is chosen from linear and branched, saturated and unsaturated, aromatic and non-aromatic, optionally substituted $C_1$-$C_{15}$ hydrocarbon-based chains, which can form at least one optionally substituted 3- to 6-membered carbon-based ring, optionally interrupted with at least one hetero atom or with at least one group bearing at least one hetero atom; the radical R'₅ is such that the atom directly linked to the quaternized nitrogen atom is a carbon atom;

R'₅ borne by the quaternized nitrogen atom, in the case of W₃, is a bond to LK;

R'₇ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2 and p" is an integer ranging from 0 to 3; wherein when the main ring does not bear the maximum number of substituents, then the unsubstituted position bears a nitrogen atom;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom; with the proviso that the group LK does not comprise any peroxo, nitro or nitroso groups or bonds; if LK is linked to W'₅, LK may end with a hetero atom or group comprising at least one hetero atom; if LK is linked to W₆, LK may end with a group comprising at least one hetero atom chosen from —CO— and —SO₂— groups; if LK is linked to W₃, the bonding takes place via a carbon atom;

wherein LK does not bear any cationic charge; and wherein the electrical neutrality of the compounds is ensured by at least one cosmetically acceptable anions (An).

24. A multi-compartment kit for dyeing keratin fibers comprising
at least one first compartment comprising at least one dye composition comprising, in a medium that is suitable for dyeing keratin fibers, as a direct dye, at least one compound chosen from those of formula (I) and the acid addition salts thereof:

Dye1-LK-Dye2 (I)

wherein Dye1 and Dye2 are chosen from:

Dye 1

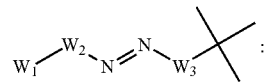

-continued

Dye 2

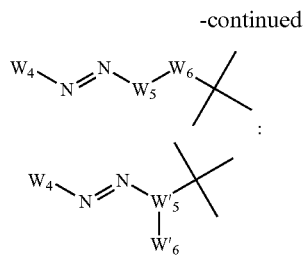

wherein:

$W_1$ and $W'_6$, which may be identical or different, are chosen from —$NR_1R_2$ and —$OR_3$ groups, wherein $R_1$, $R_2$ and $R_3$, which may be identical or different, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom; $R_1$ and $R_2$ possibly forming, with the nitrogen atom to which they are attached, an optionally substituted 5- or 7-membered heterocycle optionally comprising another nitrogen or non-nitrogen hetero atom;

$W_6$ is chosen from —$NR'_1$— groups and —O— atoms, wherein $R'_1$ is chosen from a hydrogen atom, saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom;

the radicals $R_1$, $R_2$ and $R_3$ from $W'_6$, independently of each other, may optionally form with part of the group LK and with the nitrogen or oxygen atom to which each is attached a saturated or unsaturated, aromatic or non-aromatic, optionally substituted 5- to 7-membered heterocycle;

the radical $R'_1$ from $W_6$ may optionally form, with the nitrogen atom to which it is attached and a part of the group LK, a saturated or unsaturated, aromatic or non-aromatic, optionally substituted 5- to 7-membered heterocycle optionally comprising another hetero atom chosen from nitrogen and oxygen;

$W_2$, $W_5$ and $W'_5$, which may be identical or different, are chosen from the groups of formulae (a), (b), and (c):

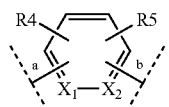
(a)

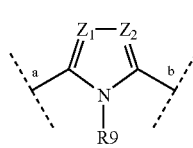
(b)

-continued

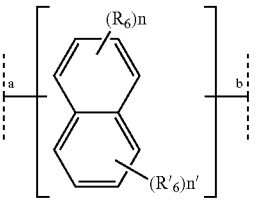
(c)

wherein:

$X_1$ is chosen from a nitrogen atom and $CR_7$ groups;
$X_2$ is chosen from a nitrogen atom and $CR_8$ groups;
$Z_1$ is chosen from a nitrogen atom and $CR_{10}$ groups;
$Z_2$ is chosen from a nitrogen atom and $CR_{11}$ groups;
$R_4$, $R_5$, $R_6$, $R'_6$, $R_7$, $R_8$, $R_{10}$ and $R_{11}$, which may be identical or different, are chosen from:

linear and branched, saturated and unsaturated, aromatic and non-aromatic, optionally substituted $C_1$-$C_{16}$ hydrocarbon-based chains, which can form at least one optionally substituted 3- to 6-membered carbon-based ring, optionally interrupted with at least one hetero atom or with at least one group bearing at least one hetero atom;

hydroxyl groups, $C_1$-$C_4$ alkoxy groups, $C_2$-$C_4$ (poly)hydroxyalkoxy groups;

alkoxycarbonyl groups (RO—CO—) in which R is chosen from $C_1$-$C_4$ alkyl radicals, alkylcarbonyloxy radicals (RCO—O—) wherein R is chosen from $C_1$-$C_4$ alkyl radicals;

amino groups, amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR—) in which the radicals R, which may be identical or different, are chosen from $C_1$-$C_4$ alkyl radicals;

carbamoyl groups (($R)_2$N—CO) in which the radicals R, which may be identical or different, are chosen from hydrogen atoms and $C_1$-$C_4$ alkyl radicals;

ureido groups (N($R)_2$—CO—NR'—) in which the radicals R and R', which may be identical or different, are chosen from hydrogen atoms and $C_1$-$C_4$ alkyl radicals;

sulfonamide groups (($R)_2$N—$SO_2$—) in which the radicals R, which may be identical or different, are chosen from hydrogen atoms and $C_1$-$C_4$ alkyl radicals;

alkylsulfonylamino groups ($RSO_2$—NR'—) in which the radicals R and R', which may be identical or different, are chosen from hydrogen atoms and $C_1$-$C_4$ alkyl radicals;

guanidinium groups (($R')_2$N—C(=$NH_2^+$)—NR—) in which the radicals R and R', which may be identical or different, are chosen from hydrogen atoms and $C_1$-$C_4$ alkyl radicals;

nitro groups; cyano groups; and halogen atoms;

wherein $R_4$, $R_5$, $R_7$, $R_8$, $R_{10}$ and $R_{11}$ may be a hydrogen atom; and wherein $R_4$, $R_5$, $R_6$, $R'_6$, $R_7$, $R_8$, $R_{10}$ and $R_{11}$, independently of each other, may optionally form, with all or some of the groups $W_1$ or $W'_6$, a saturated or unsaturated, optionally substituted 5- to 7-membered heterocycle;

a bond from $W'_5$ to $W'_6$ or to the group LK;

a is the bond from $W_2$, $W_5$ or $W'_5$ to the azo group —N=N—;

b is the bond from $W_2$ to $W_1$, from $W_5$ to $W_6$, or from $W'_5$ to $W'_6$;

$R_9$ is chosen from:
a hydrogen atom,
linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

wherein when the sum of n and n' is less than 6, each missing substituent is a hydrogen atom;

$W_3$ and $W_4$, which may be identical or different, are cationic heteroaromatic radicals chosen from those of formulae (1) to (11):

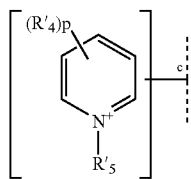
(1)

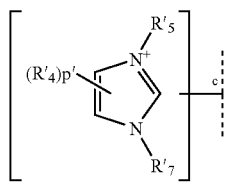
(2)

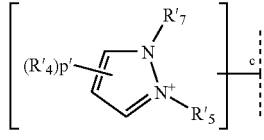
(3)

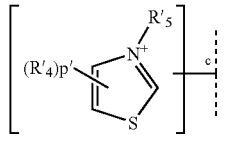
(4)

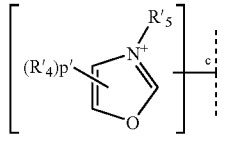
(5)

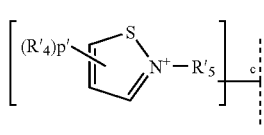
(6)

-continued

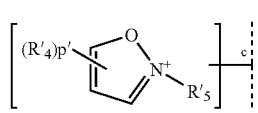
(7)

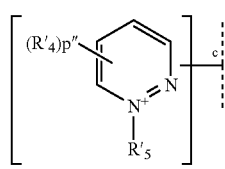
(8)

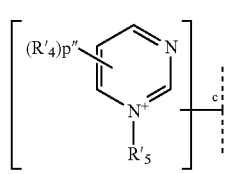
(9)

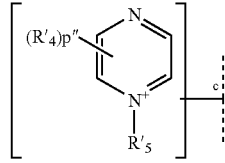
(10)

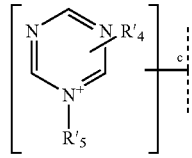
(11)

wherein:
$R'_4$, which may be identical or different, substituting the main ring, are chosen from:
linear and branched, saturated and unsaturated, aromatic and non-aromatic, optionally substituted $C_1$-$C_{16}$ hydrocarbon-based chains, which can form at least one 3- to 6-membered carbon-based rings, optionally interrupted with at least one hetero atom or with at least one group bearing at least one hetero atom;

hydroxyl groups, $C_1$-$C_4$ alkoxy groups, $C_2$-$C_4$ (poly)hydroxyalkoxy groups;

alkoxycarbonyl groups (RO—CO—) in which R is chosen from $C_1$-$C_4$ alkyl radicals, alkylcarbonyloxy radicals (RCO—O—) in which R is chosen from $C_1$-$C_4$ alkyl radicals;

amino groups, amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR'—) in which the radical R is chosen from $C_1$-$C_4$ alkyl radicals and the radical R' is chosen from a hydrogen atom and $C_1$-$C_4$ alkyl radicals;

carbamoyl groups (($R)_2N—CO—$) in which the radicals R, which may be identical or different, are chosen from hydrogen atoms and $C_1$-$C_4$ alkyl radicals;

ureido groups ($N(R)_2—CO—NR'—$) in which the radicals R and R', which may be identical or different, are chosen from hydrogen atoms and $C_1$-$C_4$ alkyl radicals;

sulfonamide groups (($R)_2N—SO_2—$) in which the radicals R, which may be identical or different, are chosen from hydrogen atoms and $C_1$-$C_4$ alkyl radicals;

alkylsulfonylamino groups ($RSO_2—NR'—$) in which the radicals R and R', which may be identical or different, are chosen from hydrogen atoms and $C_1$-$C_4$ alkyl radicals;

guanidinium groups (($R')_2N—C(=NH_2^+)—NR—$) in which the radicals R and R', which may be identical or different, are chosen from hydrogen atoms and $C_1$-$C_4$ alkyl radicals;

nitro groups; cyano groups; and halogen atoms;

wherein two radicals $R'_4$ borne by two adjacent carbon atoms of the main ring may optionally form an aromatic or non-aromatic, 5- or 6-membered secondary ring, optionally substituted with at least one entity chosen from hydrogen atoms, hydroxyl groups, $C_1$-$C_4$ alkyl radicals, a $C_1$-$C_4$ alkoxy radicals, $C_2$-$C_4$(poly)hydroxyalkoxy radicals, amino radicals, and amino radicals substituted with at least one or more $C_1$-$C_4$ alkyl radical, which may be identical or different, optionally bearing at least one hydroxyl group;

$R'_5$, borne by the quaternized nitrogen atom, in the case of $W_4$, is chosen from linear and branched, saturated and unsaturated, aromatic and non-aromatic, optionally substituted $C_1$-$C_{16}$ hydrocarbon-based chains, which can form at least one optionally substituted 3- to 6-membered carbon-based rings, optionally interrupted with at least one hetero atom or with at least one group bearing at least one hetero atom; the radical $R'_5$ is such that the atom directly linked to the quaternized nitrogen atom is a carbon atom;

$R'_5$ borne by the quaternized nitrogen atom, in the case of $W_3$, is a bond to LK;

$R'_7$ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2 and p" is an integer ranging from 0 to 3; wherein when the main ring does not bear the maximum number of substituents, then the unsubstituted position bears a nitrogen atom;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom; with the proviso that the group LK does not comprise any peroxo, nitro or nitroso groups or bonds; if LK is linked to $W'_5$, LK may end with a hetero atom or group comprising at least one hetero atom; if LK is linked to $W_6$, LK may end with a group comprising at least one hetero atom chosen from —CO— and —$SO_2$— groups; if LK is linked to $W_3$, the bonding takes place via a carbon atom;

wherein LK does not bear any cationic charge; and wherein the electrical neutrality of the compounds is ensured by at least one cosmetically acceptable anions (An), and at least one second compartment comprising at least one oxidizing composition comprising at least one oxidizing agent.

\* \* \* \* \*

UNITED STATES PATENT AND TRADEMARK OFFICE
CERTIFICATE OF CORRECTION

PATENT NO.       : 7,288,122 B2
APPLICATION NO.  : 11/159242
DATED            : October 30, 2007
INVENTOR(S)      : Andrew Greaves et al.

It is certified that error appears in the above-identified patent and that said Letters Patent is hereby corrected as shown below:

On the Title Page, Item (75), in the Inventors, line 2, "Hervé David, Joinville le Pont (FR)" should read --Hervé David, La Varenne St Hilaire (FR)--

In claim 1, column 34, line 39, "$R_1$, is chosen" should read --$R_1$ is chosen--.

In claim 1, column 38, lines 35-36, "a $C_1$-$C_4$ alkoxy radicals," should read --$C_1$-$C_4$ alkoxy radicals,--.

In claim 1, column 38, line 38, "one or more $C_1$-$C_4$ alkyl radical," should read --one or more $C_1$-$C_4$ alkyl radicals,--.

In claim 7, column 40, line 49, "formula (a) and (c)." should read --formulae (a) and (c).--.

In claim 13, column 43, lines 25-26, "one cosmetically acceptable anions" should read --one cosmetically acceptable anion--.

In claim 15, column 43, line 65, "one groups" should read --one group--.

In claim 15, column 45, line 51, "$R_{11}$, may" should read --$R_{11}$ may--.

In claim 15, column 45, line 53, "$R_4$, -$R_5$," should read --$R_4$, $R_5$,--.

In claim 15, column 47, line 62, "groups (R)$_2$N-SO$_2$-)" should read --groups ((R)$_2$N-SO$_2$-)--.

In claim 15, column 48, line 58, "one cosmetically acceptable anions" should read --one cosmetically acceptable anion--.

In claim 18, column 49, line 4, "comprising at least one at least one color modifier" should read --comprising at least one color modifier--.

In claim 19, column 49, line 12, "berizoquinone," should read --benzoquinone,--.

In claim 23, column 50, line 51, "$R_{11}$ which" should read --$R_{11}$, which--.

In claim 23, column 50, line 55, "$C_1$-$C_{15}$ hydrocarbon-based chains," should read --$C_1$-$C_{16}$ hydrocarbon-based chains,--.

UNITED STATES PATENT AND TRADEMARK OFFICE
CERTIFICATE OF CORRECTION

PATENT NO.       : 7,288,122 B2
APPLICATION NO.  : 11/159242
DATED            : October 30, 2007
INVENTOR(S)      : Andrew Greaves et al.

It is certified that error appears in the above-identified patent and that said Letters Patent is hereby corrected as shown below:

In claim 23, column 51, line 56, "$C_1$-$C_{15}$ hydrocarbon-based chains," should read --$C_1$-$C_{16}$ hydrocarbon-based chains,--.

In claim 23, column 53, line 16, "$C_1$-$C_{15}$ hydrocarbon-based chains," should read --$C_1$-$C_{16}$ hydrocarbon-based chains,--.

In claim 23, column 54, line 10, "$C_1$-$C_{15}$ hydrocarbon-based chains," should read --$C_1$-$C_{16}$ hydrocarbon-based chains,--.

In claim 23, column 54, line 48, "one cosmetically acceptable anions" should read --one cosmetically acceptable anion--.

In claim 24, column 59, lines 27-28, "a $C_1$-$C_4$ alkoxy radicals," should read --$C_1$-$C_4$ alkoxy radicals,--.

In claim 24, column 59, line 30, "one or more $C_1$-$C_4$ alkyl radical," should read --one or more $C_1$-$C_4$ alkyl radicals,--.

In claim 24, column 60, line 33, "one cosmetically acceptable anions" should read --one cosmetically acceptable anion--.

Signed and Sealed this

Third Day of June, 2008

JON W. DUDAS
*Director of the United States Patent and Trademark Office*